US011234616B2

(12) United States Patent
Herr

(10) Patent No.: US 11,234,616 B2
(45) Date of Patent: Feb. 1, 2022

(54) MECHANISMS AND METHODS FOR THE DESIGN AND FABRICATION OF A MECHANICAL INTERFACE BETWEEN A WEARABLE DEVICE AND A HUMAN BODY SEGMENT

(71) Applicant: Bionic Skins LLC, Lebanon, NH (US)

(72) Inventor: Hugh M. Herr, Somerville, MA (US)

(73) Assignee: BIONIC SKINS LLC, Lebanon, NH (US)

(*) Notice: Subject to any disclaimer, the term of this patent is extended or adjusted under 35 U.S.C. 154(b) by 1717 days.

(21) Appl. No.: 14/838,985

(22) Filed: Aug. 28, 2015

(65) Prior Publication Data

US 2016/0058519 A1    Mar. 3, 2016

Related U.S. Application Data

(60) Provisional application No. 62/043,842, filed on Aug. 29, 2014.

(51) Int. Cl.
*A61B 5/107* (2006.01)
*A61B 90/00* (2016.01)
(Continued)

(52) U.S. Cl.
CPC ............ *A61B 5/1078* (2013.01); *A61B 5/107* (2013.01); *A61B 34/10* (2016.02); *A61F 2/5044* (2013.01);
(Continued)

(58) Field of Classification Search
CPC ....... A61B 5/1078; A61B 5/107; A61B 19/50; A61B 2019/502; A61B 2019/464;
(Continued)

(56) References Cited

U.S. PATENT DOCUMENTS 5,012,817 A * 5/1991 Zeilinski ................ A61B 5/225
                                                    600/557
6,322,515 B1 * 11/2001 Goor .................. A61B 5/02007
                                                    600/481

(Continued)

FOREIGN PATENT DOCUMENTS

WO    2007144608 A2    12/2007
WO    2013142343 A1     9/2013

OTHER PUBLICATIONS

Carter, F.J., Frank, T.G., Davies, P.J., McLean, D., Cushieri, A., "Measurements and modelling of the compliance of human and porcine organs", Medical Image Analysis 5 (2001) 231-236, Elsevier Science B.V., 2001.

*Primary Examiner* — Oommen Jacob
*Assistant Examiner* — Shahdeep Mohammed
(74) *Attorney, Agent, or Firm* — Barlow, Josephs & Holmes, Ltd.; David R. Josephs

(57) ABSTRACT

The system includes an instrument for determining the anatomical, biomechanical, and physiological properties of a body segment that includes one or more force sensitive probes is provided. A human operator actuates one or more force sensitive probes, wherein the force sensitive probes are positioned at the surface of the body segment. The operator pushes on the force sensitive probes with varying force applied on the body segment to measure tissue deflection forces. The instrument may include one or more of gyroscopes, accelerometers, and magnetometers capable of measuring changes in tissue deflection caused by the force sensitive probes relative to a grounded reference frame in 3-D space, wherein the tissue deflection force data and the change in tissue deflection data are used to compute segment tissue viscoelastic properties. The instrument may also be untethered or wireless.

15 Claims, 14 Drawing Sheets
(13 of 14 Drawing Sheet(s) Filed in Color)

(51) Int. Cl.
*A61F 2/76* (2006.01)
*A61F 2/50* (2006.01)
*A61F 2/78* (2006.01)
*A61B 34/10* (2016.01)

(52) U.S. Cl.
CPC .............. *A61F 2/76* (2013.01); *A61F 2/7812* (2013.01); *A61B 2034/102* (2016.02); *A61B 2090/064* (2016.02); *A61B 2560/0425* (2013.01); *A61B 2562/0219* (2013.01); *A61B 2562/0223* (2013.01); *A61B 2562/0261* (2013.01); *A61F 2002/762* (2013.01)

(58) Field of Classification Search
CPC .... A61B 2562/0261; A61B 2562/0223; A61B 2562/0219; A61B 2560/0425
See application file for complete search history.

(56) References Cited

U.S. PATENT DOCUMENTS

| | | | |
|---|---|---|---|
| 6,511,427 B1* | 1/2003 | Sliwa, Jr. | A61B 5/4869 600/438 |
| 2005/0119568 A1* | 6/2005 | Salcudean | A61B 8/08 600/437 |
| 2008/0119737 A1* | 5/2008 | Urbano | A61B 8/00 600/459 |
| 2009/0012430 A1* | 1/2009 | Lovoi | G16H 50/50 600/586 |
| 2009/0076732 A1 | 3/2009 | Sprigle et al. | |
| 2009/0264894 A1* | 10/2009 | Wasielewski | A61F 2/389 606/102 |
| 2010/0331738 A1* | 12/2010 | Stein | A61B 5/103 600/587 |
| 2011/0172565 A1* | 7/2011 | Shih | G01N 29/0672 600/587 |
| 2013/0197318 A1 | 8/2013 | Herr et al. | |
| 2013/0217998 A1* | 8/2013 | Mahfouz | A61B 5/0059 600/409 |
| 2013/0282141 A1* | 10/2013 | Herr | A61F 2/5046 623/33 |
| 2014/0052026 A1 | 2/2014 | Bishara et al. | |
| 2014/0094701 A1 | 4/2014 | Kwartowitz et al. | |

* cited by examiner (Detail A)　　　　　　　(Detail B)

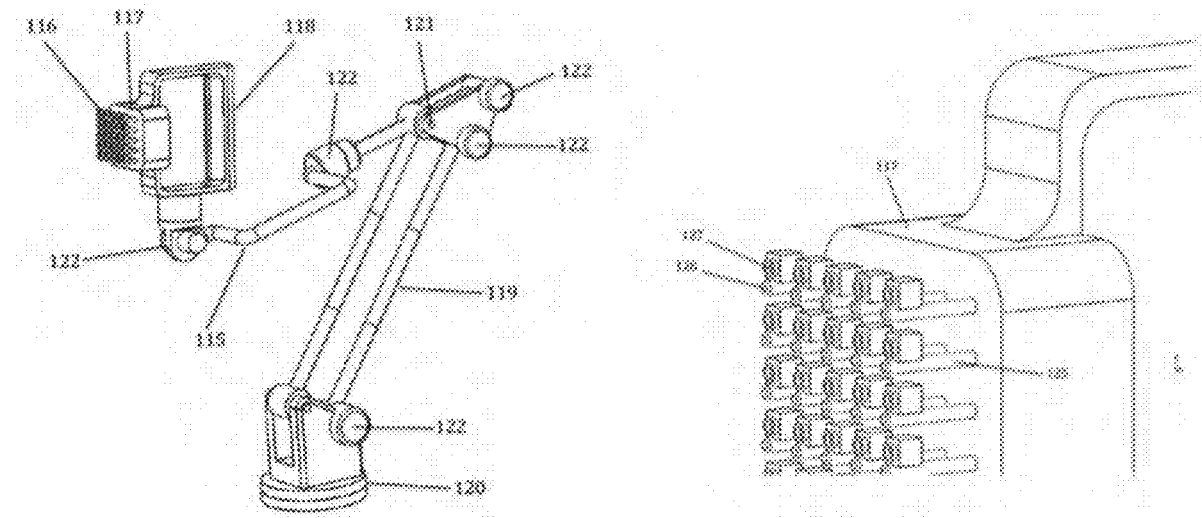
Fig. 10A
Fig. 10B
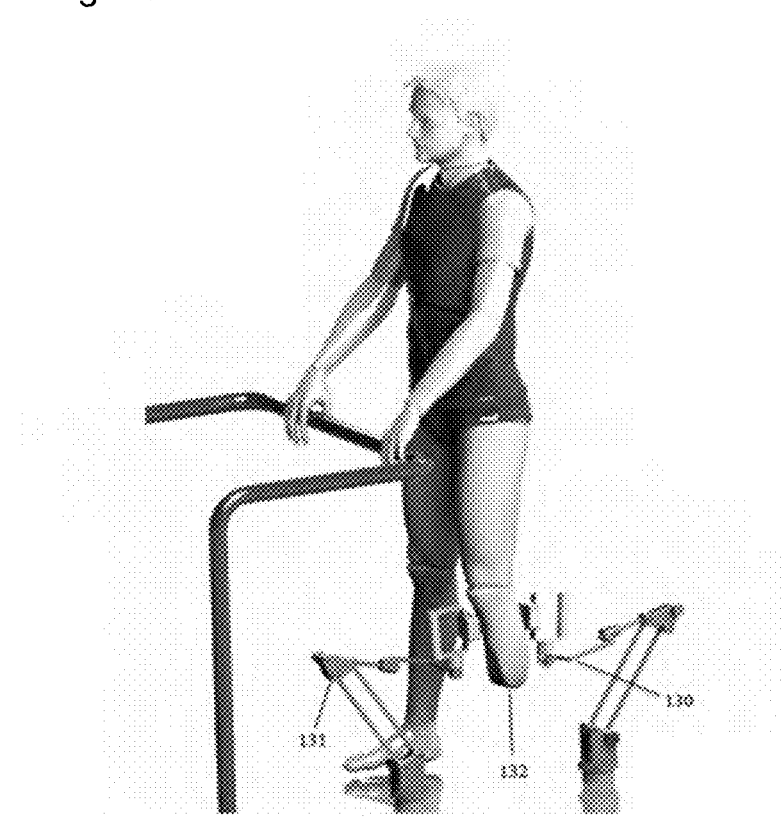
Fig. 11

Fig. 19
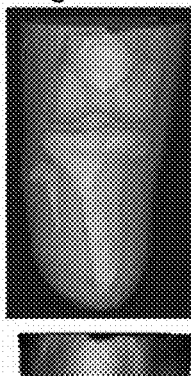
Fig. 20A
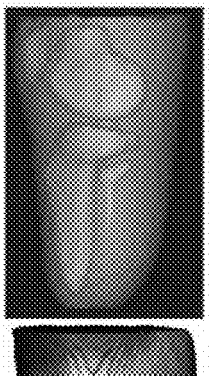
Fig. 20B
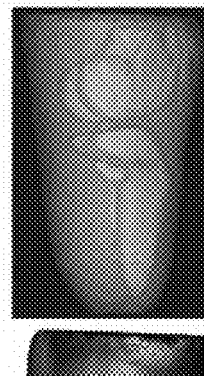
Fig. 20C
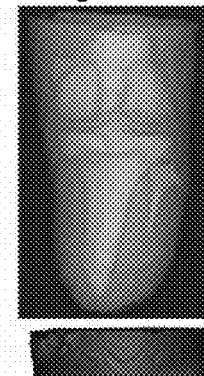
Fig. 20D
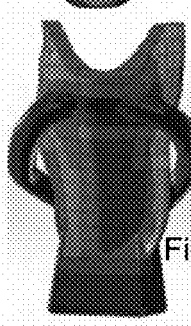
Fig. 20E
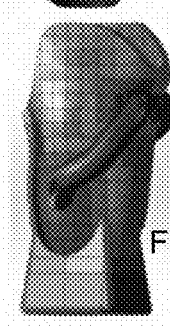
Fig. 20F
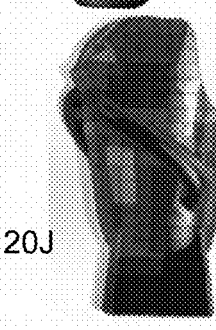
Fig. 20G
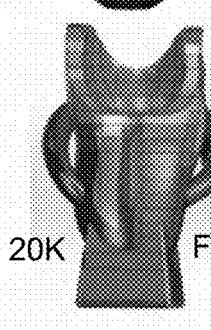
Fig. 20H
Fig. 20I
Fig. 20J
Fig. 20K
Fig. 20L
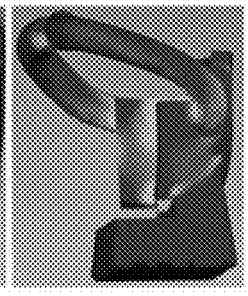
Fig. 20M
Fig. 20N
Fig. 20O
Fig. 20P Table 1
| Soft Tissue Depth (mm) | Color | Socket Tensile Strength (MPa) | Color |
|---|---|---|---|
| 0 – 9 | | 0.5 – 1.5 | |
| 9 – 13 | | 8 – 12 | |
| 13 – 16 | | 12 – 14 | |
| 16 – 20 | | 14 – 20 | |
| 20 – 50 | | 50 – 65 | |
Fig. 31
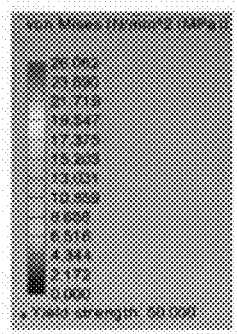
Fig. 21
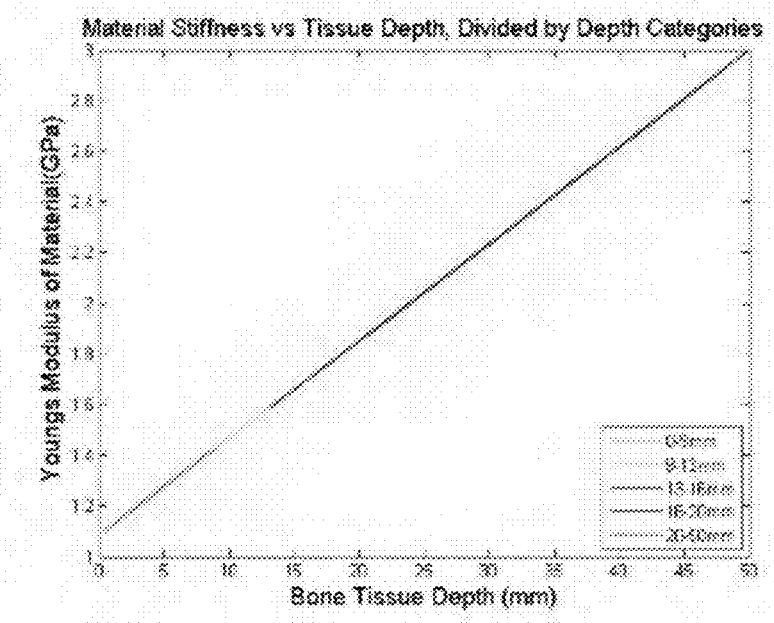
Fig. 22

MECHANISMS AND METHODS FOR THE DESIGN AND FABRICATION OF A MECHANICAL INTERFACE BETWEEN A WEARABLE DEVICE AND A HUMAN BODY SEGMENT

CROSS REFERENCE TO RELATED APPLICATION

This application is related to and claims priority from earlier filed provisional patent application Ser. No. 62/043,842, filed Aug. 29, 2014, the entire contents thereof is incorporated herein by reference.

BACKGROUND OF THE INVENTION

This invention relates generally to the design and fabrication of a mechanical interface that connects a human body segment to wearable technology such as shoes, bras, apparel, seats, limb prostheses, limb orthoses or body exoskeletal devices. Conventional design and fabrication strategies for a mechanical interface employ an incomplete data representation of the relevant human body segment, a non-quantitative methodology to determine the corresponding interface design, and inadequate fabrication techniques to construct the final product.

To design and fabricate a socket for a prosthetic limb, for example, a prosthetist first takes a mold of the residual limb, capturing its 3-D shape. Depending on the practitioner's preference, this molding process is performed when the relevant human body segment is either in a loaded or unloaded state. The measurement of residual limb shape is most typically performed using a plaster-impregnated gauze that is first dipped into water and then wrapped around the residual limb. Once wrapped, the plaster hardens to form a female cup that is then poured with plaster to form a male plug with the residual limb's shape. The prosthetist then removes plaster in soft tissue regions where he/she wants the final socket interface to compress the residual limb tissue, and adds plaster around sensitive regions to create a void in the final socket wall. Once these craft modifications are complete, a final carbon composite or thermoplastic socket is fabricated over the male plug. As an example, in FIGS. 1A and 1B, different views of a plaster male plug 30 of a below-knee residual limb is shown after a prosthetist had completed modifications to the unloaded shape, and in FIGS. 2A and 2B, different views of the final, carbon-fiber transtibial socket 32 is shown, fabricated using the plaster male plug 30 shown in FIGS. 1A and 1B. The residual biological limb is then inserted into the carbon socket, with a often silicone liner and socks worn on the residual limb to cushion the limb and to minimize skin-interface chaffing.

More specifically, FIGS. 1A and 1B, for a transtibial patient, show a plaster male plug 30 after regions of soft tissue had been reduced from the original residual-limb shape, and sensitive regions expanded upon.

In FIG. 2A, an anterior view of the final carbon transtibial socket 32 is shown while FIG. 2B shows an internal view of the same socket 32, depicting internal craft modifications performed by a prosthetist to optimize comfort. To construct the socket 32, a prosthetist fabricates carbon materials over the male plug shown in FIGS. 1A and 1B.

It is well known in the art, as this particular example illustrates, today's design and fabrication strategies for mechanical interfaces employ an incomplete data representation of the relevant human body segment, and a non-quantitative methodology to determine the corresponding interface design. Furthermore, today's interface fabrication strategies do not allow for continuously varying material properties within the interface that reflect the multi-tissue, continuously-varying, viscoelastic properties of the underlying anatomy for which the mechanical interface is designed to intimately connect. Such a poor correspondence between body and synthetic interface causes discomfort for the wearer due to excessive pressures, internal strains, shear forces and skin chaffing between the attached device, clothing or shoe article, and the human body segment.

As noted earlier, practitioners typically measure the shape of the human limb segment of interest, and then modify that shape using non-quantitative craft techniques that do not quantitatively map the underlying anatomical, biomechanical and physiological features to tissue compression levels and internal stresses and strains imposed by the interface. Moreover, the final interface is typically homogenious, or nearly homogenious, in terms of its viscoelastic properties, spatially and temporally; for example, the carbon fiber socket shown in FIG. 2 is rigid across the entire interface surface, and that rigidity is invariant in time. Further, the silicone liner worn directly against the residual skin is also typically homogeneous, or nearly so, in terms of its viscoelastic properties.

Attempts have been made to vary the viscoelastic properties of the interface spatially using a 'windowing' approach where holes are cut into a rigid, external interface wall to allow an intermediate, softer material to penetrate through the window upon load bearing applied to the interface. However, such windowing techniques use separate distinct material components resulting in an interface that does not reflect the continuously-varying human body viscoelastic properties found in the underlying anatomy. Further, often the tensile elasticity of the silicone liner, worn on the residual limb in the case of leg amputation, is varied somewhat spatially so as to stiffen the liner against axial, longitudinal stretch, but to still allow compliance for circumferential tensile strains. However, these liner impedance variations do not reflect the multi-tissue, continuously-varying, viscoelastic properties of the underlying anatomy.

In view of the foregoing, there is a demand for a system that can more effectively and accurately determine the anatomical, biomechanical, and physiological properties of a body segment in order to provide a superior mechanical interface between a wearable device and human body segment.

SUMMARY OF THE INVENTION

The present invention preserves the advantages of prior art mechanisms and methods for the design and fabrication of a mechanical interface between a wearable device and a human body segment. In addition, it provides new advantages not found in currently available mechanisms and methods and overcomes many disadvantages of such currently available mechanisms and methods.

The invention is generally directed to an instrument, preferably untethered, for determining the anatomical, biomechanical, and physiological properties of a body segment that includes one or more force sensitive probes, a human operator to actuate the one or more force sensitive probes, wherein the one or more force sensitive probes are positioned at the surface of the body segment and the operator then pushes on the one or more force sensitive probes with varying force applied on the body segment to measure tissue deflection forces, wherein the untethered instrument further comprises one or more of gyroscopes, accelerometers, and magnetometers capable of measuring changes in tissue deflection caused by the one or more force sensitive probes relative to a grounded reference frame in 3-D space, wherein the tissue deflection force data and the change in tissue deflection data are used to compute segment tissue viscoelastic properties.

It is therefore an object of the present invention to provide a system includes an instrument for determining the anatomical, biomechanical, and physiological properties of a body segment that includes one or more force sensitive probes is provided.

A further object of the present invention is to enable a human operator to actuates one or more force sensitive probes, wherein the force sensitive probes are positioned at the surface of the body segment where the operator pushes on the force sensitive probes with varying force applied on the body segment to measure tissue deflection forces.

Yet another object of the present invention is to provide an instrument may include one or more of gyroscopes, accelerometers, and magnetometers capable of measuring changes in tissue deflection caused by the force sensitive probes relative to a grounded reference frame in 3-D space, wherein the tissue deflection force data and the change in tissue deflection data are used to compute segment tissue viscoelastic properties.

Yet a further object of the present invention is to provide an instrument that is untethered or wireless.

BRIEF DESCRIPTION OF THE DRAWINGS

The patent or application file contains at least one drawing executed in color. Copies of this patent or patent application publication with color drawing(s) will be provided by the Patent and Trademark Office upon request and payment of the necessary fee.

The novel features which are characteristic of the present invention are set forth in the appended claims. However, the invention's preferred embodiments, together with further objects and attendant advantages, will be best understood by reference to the following detailed description taken in connection with the accompanying drawings in which:

FIGS. 10A and 10B show different views of a probe array on a flexible arm;

FIG. 11 shows two probe arrays on flexible arms collecting anatomical, biomechanical and physiological data of a transtibial residual limb;

FIG. 19 is a perspective view of a 3D printer;

FIGS. 20A-20D show MRI images for the right leg of a transtibial amputee;

FIGS. 20E-20H show images of the soft tissue depth model of the residual limb;

FIGS. 20I-20L show a 3-D printed prosthetic socket where every material color corresponds to a material having a distinct durometer and tensile strength;

FIGS. 20M-20P show the socket's most rigid, high tensile strength material being is modeled;

FIG. 21 shows The Von Mises Stress distribution for finite element analyses shown in the fourth row shown in FIGS. 20M-20P;

FIG. 22 is a graph mapping between the Young's Modulus of socket interface materials shown in the third row of FIGS. 20I-20L to the soft tissue depth at each location shown in the second row of FIGS. 20E-20H, which is color coded by categories of soft tissue depth;

FIG. 31 is a table (Table 1) showing the color mapping used in FIG. 15.

DETAILED DESCRIPTION OF THE INVENTION

Figure 1A:
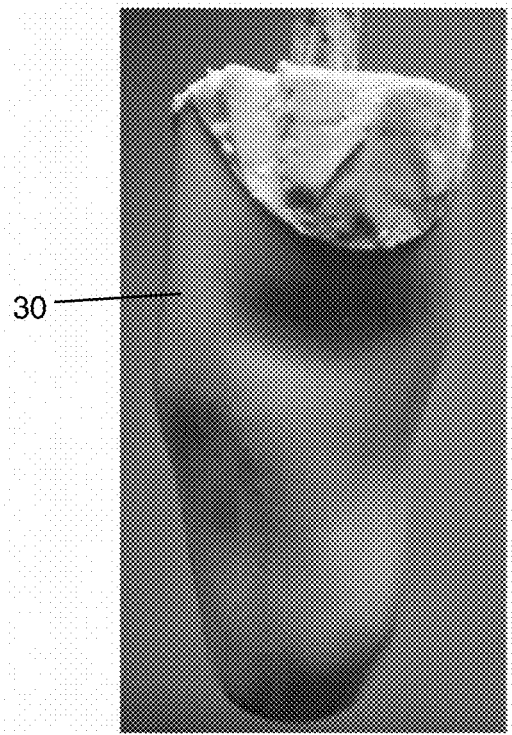
FIGS. 1A and 1B show, for a transtibial patient, different views of a plaster male plug is shown after regions of soft tissue had been reduced from the original residual-limb shape, and sensitive regions expanded upon.
Figure 1B:
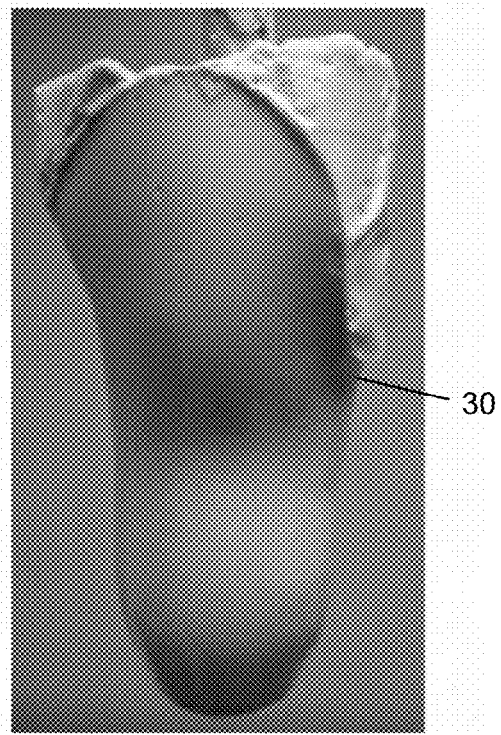
Figure 2A:
FIG. 2A shows and external anterior view of the final carbon transtibial socket.
Figure 2B:
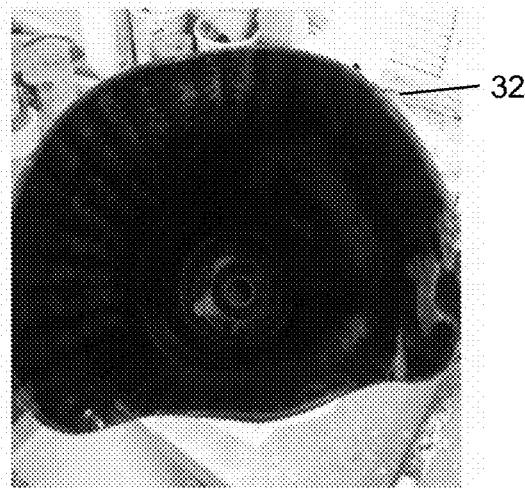
FIG. 2B shows an internal view of the socket of FIG. 2A.

In accordance with the present invention, as a resolution to the difficulties discussed above, a quantitative methodology is presented that relates human-body anatomical, biomechanical and physiological properties to the design and fabrication of a novel mechanical interface. Specifically, the present invention describes a quantitative, scientific methodology that relates measurements of biological segment shape, skin strain characteristics resulting from body movement, viscoelastic tissue properties for state disturbances perpendicular to the bodies surface, sensitivities to applied pressure due to bursitis, nerve, blood flow restrictions, chronic wounds, etc., vascularization and peripheral nerve anatomy, and the like, to the corresponding interface shape and impedance characteristics, spatially and temporally. It will be understood by those of ordinary skill in the art that the methodologies presented in herein could be employed in the mechanical-interface design and fabrication of any wearable article or mechanism, including shoes, cloths, seats, bras, prostheses, orthoses or exoskeletons.

The design and fabrication methodologies of the present invention are divided into three different phases or steps. The first step comprises acquiring a comprehensive data set of the relevant human body segment's underlying anatomy, biomechanics and physiology, and then processing these data to build a digital representation, or model, of the biological segment for which the mechanical interface will connect. Next, in a second step, a quantitative mapping from the biological model to an interface model is generated. The interface model is a digital representation of interface shape and impedance properties. Finally, in a third step, the interface model is used to fabricate either a test interface, or the final interface to be used by the wearer of the article or mechanism.

Step 1: Biological Data Acquisition and Modeling

In accordance with the present invention, the first part to the production of a mechanical interface includes collecting anatomical, biomechanical and physiological data that can be used to develop a model of the biological segment of interest. Such a model is necessary to describe the relevant biological segment's properties, including but not limited to its shape, skin strain characteristics resulting from body movement, viscoelastic tissue properties for state disturbances perpendicular to the bodies surface, sensitivities to applied pressure due to bursitis, nerve, blood flow restrictions, chronic wounds, and the like, all as a function of anatomical location. Such a data-driven model can be represented as a vector of biological properties at each anatomical location across the body segment for which an article of clothing, a worn shoe, or a wearable device is designed to interface.

Data Types and Methods of Acquisition

Skin Strain

A critical data set relevant to the design of a mechanical interface is skin strain dynamics caused by body joint movements. A procedure is outlined in this section that can be used to collect data necessary to estimate the skin strain field of the biological segment of interest, and then to compute the skin strain field as a function of limb posture. Such information is necessary to understand how the mechanical interface should move and stretch relative to the skin surface, so as to minimize shear forces and discomfort at the skin-interface junction.

In this procedure, the biological limb is first marked with a matrix of small (~2 mm diameter), black-ink dots across the entire skin-surface area for which the interface is designed to interact. The specific anatomical location and distance between these dots need not be precise, but the resolution, or the number of dots per $cm^2$ is important, as this resolution defines the resolution of the resulting skin strain field. Further, the pattern of dots should be randomized, providing the opportunity to create a unique skin speckle pattern for each anatomical region. With such a patterning, a single camera image taken of a small region of the skin surface can be used to determine the anatomical position at which the camera's lens is pointed or directed. Such an anatomical-positioning algorithm can be achieved by comparing the single, anatomically-local image to the full speckle patterns across the entire biological segment. As an alternative to a matrix of small dots, the skin of the biological segment of interest can be speckled with a sponge where the sponge is first dipped in FDA approved body paint. By dabbing the painted sponge across the skin surface, a unique pattern of skin speckles can be created.

Next, separate poses, or joint postures of the biological segment of interest, are captured using photogrammetric tools. Using approximately 30 digital photographs for each limb pose, 3D models can be generated.

The coordinates of the black dots on the skin are marked and exported for analysis. The point clouds for each pose are triangulated in a corresponding manner so the mapping of points to triangles is the same. In FIG. 3, an example is shown for a transtibial amputee's residual limb showing three levels of knee flexion, and a matrix of black dots across the skin surface.

Figure 3A:
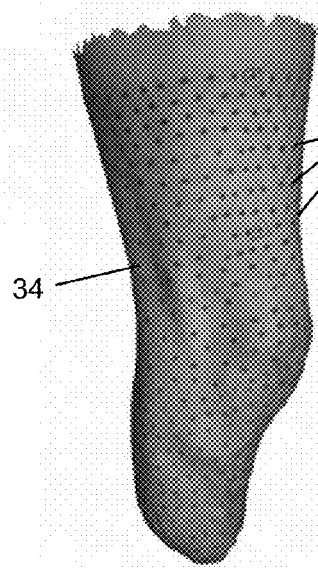
FIGS. 3A-C show three poses of a transtibial residual limb corresponding to a particular knee flexion angle.
Figure 3B:
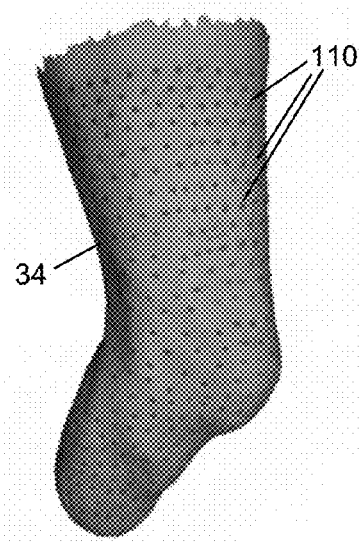
Figure 3C:
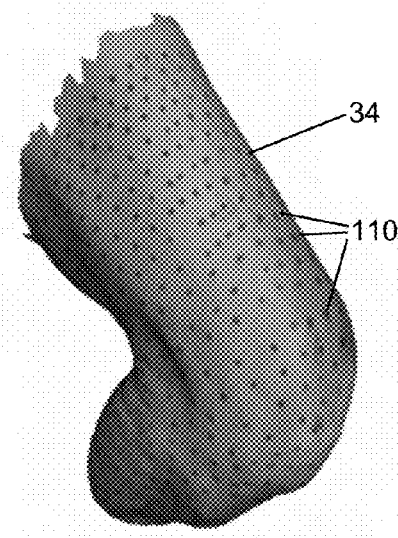

Referring now to FIGS. 3A-C, three different poses of a transtibial residual limb 34 are shown each corresponding to a particular knee flexion angle. Black dots 110 mark the skin at a resolution of approximately 4 dots per $cm^2$.

Figure 4A:
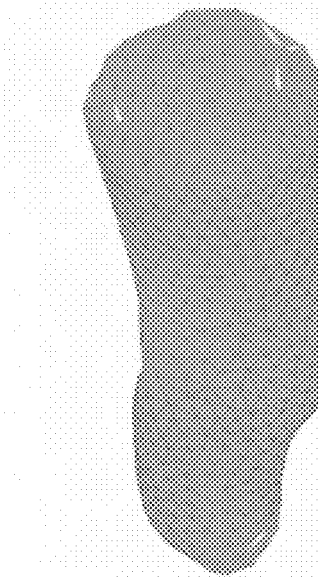
FIGS. 4A-C show the coordinate information from three triangulated poses of a transtibial residual limb of FIG. 3AC that are used to compute the strain transforms.
Figure 4B:
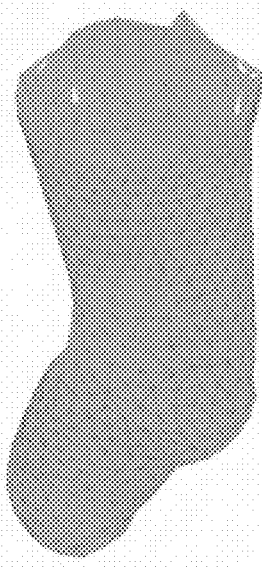
Figure 4C:
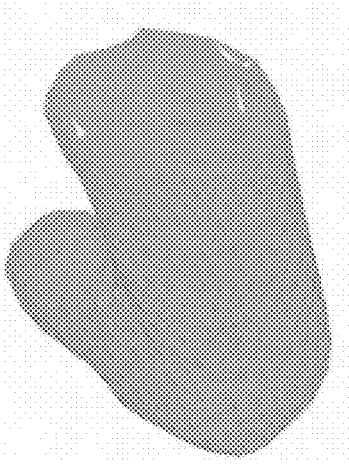

The black dots 110 are the nodes of the finite element model and serve as the vertices for the surface triangulation. FIGS. 4A-C show the respective triangulated surface corresponding to the poses displayed in FIGS. 3A-C.

Further, FIGS. 4A-C show the coordinate information from three triangulated poses of a transtibial residual limb are used to compute the strain transforms. A constant strain element analysis is performed on each triangle to ascertain the strain field of the limb's surface.

The deformation of each triangular element from one pose to another is decomposed into a translation, rotation, and stretch via an affine transform. The three initial coordinate pairs $(x_i, y_i)$ and three final coordinate pairs $(x_f, y_f)$ are used to find the affine transform linking the two limb poses. Equation 1 represents the affine transformation matrix that links the point sets for each element. The rigid body translation from the initial to the final pose ($\Delta x, \Delta y$) is neglected as it has no effect on the strain within the element.

$$\begin{bmatrix} x_f \\ y_f \\ 1 \end{bmatrix} = \begin{bmatrix} & & \Delta x \\ & A & \\ & & \Delta y \\ 0 & 0 & 1 \end{bmatrix} \begin{bmatrix} x_i \\ y_i \\ 1 \end{bmatrix} \quad (1)$$

The matrix A is a 2×2 matrix that contains the information about how a particular triangle is rotated and stretched. A singular value decomposition (SVD) of matrix A isolates the components of the deformation as described by equation 2. The SVD interprets the transformation as a rotation V* to the principal coordinate frame, followed by a stretch Σ along those axes, and an additional rotation U to the final coordinate frame.

$$A = U\Sigma V^* \qquad (2)$$

The stretch matrix yields the principal strains which are used to compute the average strain of each constant strain triangle. Equation 3 computes the von Mises or equivalent strain $\varepsilon_e$ from the principal strains, $\varepsilon_1$ and $\varepsilon_2$. FIG. 5 shows the equivalent strain of each triangulation resulting from the deformation of the original, extended pose to two different levels of knee flexion. The average strain is a scalar value that is useful for assessing the overall stretch of an element.

$$\varepsilon_e = \frac{1}{2}\sqrt{(\varepsilon_1 - \varepsilon_2)^2 + \varepsilon_1^2 + \varepsilon_2^2} \qquad (3)$$

Furthermore, the strain state of each two-dimensional surface element can be derived from Mohr's circle using the principal strain information. This maps the two principal strains to a combination of normal and shear strains in another coordinate frame.

Figure 5A:
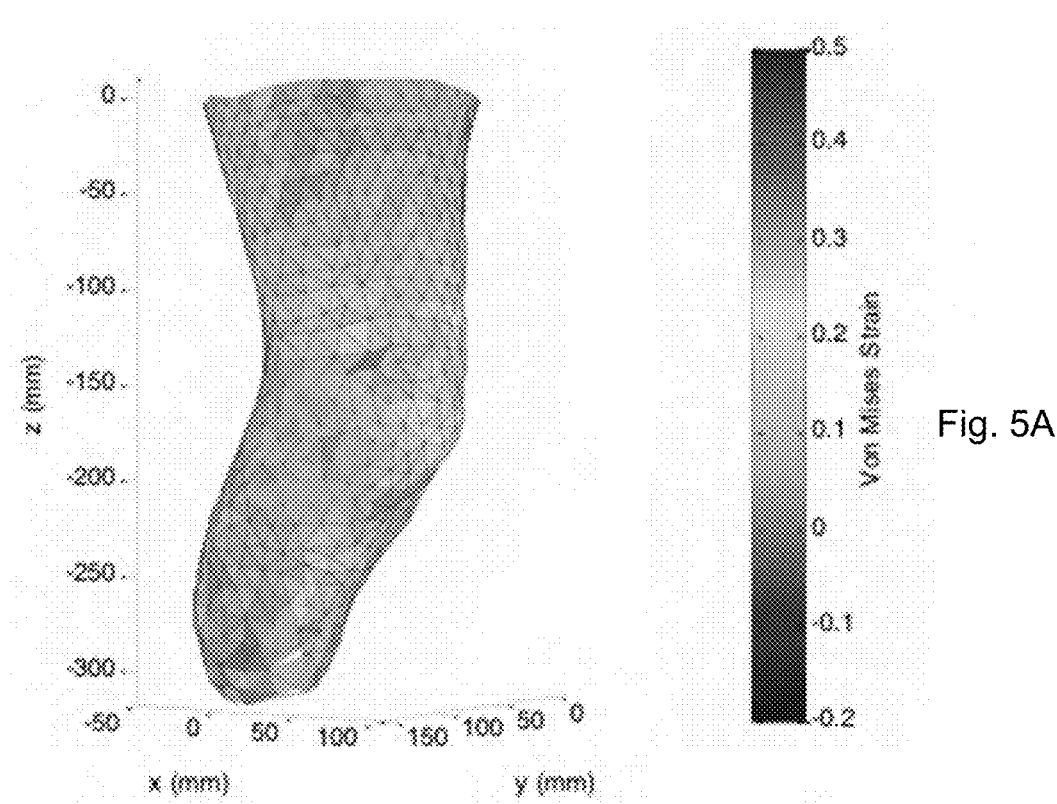
FIG. 5A shows the average strain of each triangular face being analyzed and mapped to a color, where the skin strain levels are shown for the partially flexed pose.
Figure 5B:
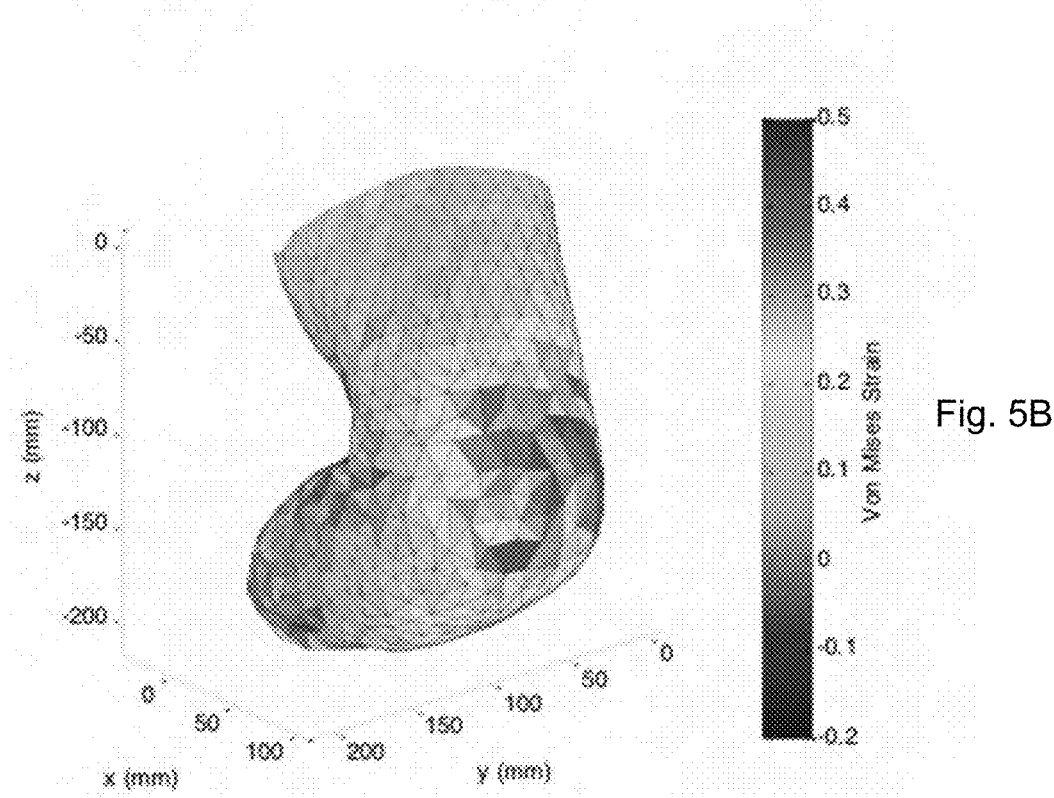
FIG. 5B shows the average strain of each triangular face being analyzed and mapped to a color, wherein skin strain levels are shown for the fully flexed pose.

The average strain of each triangular face is analyzed and mapped to a color. Skin strain levels are shown for the partially flexed pose, as shown in the plot of FIG. 5A, and the fully flexed pose, as shown in the plot of FIG. 5B. Here higher average strain is shown around the knee patella due to the right pose's increased knee flexion.

Figure 6A:
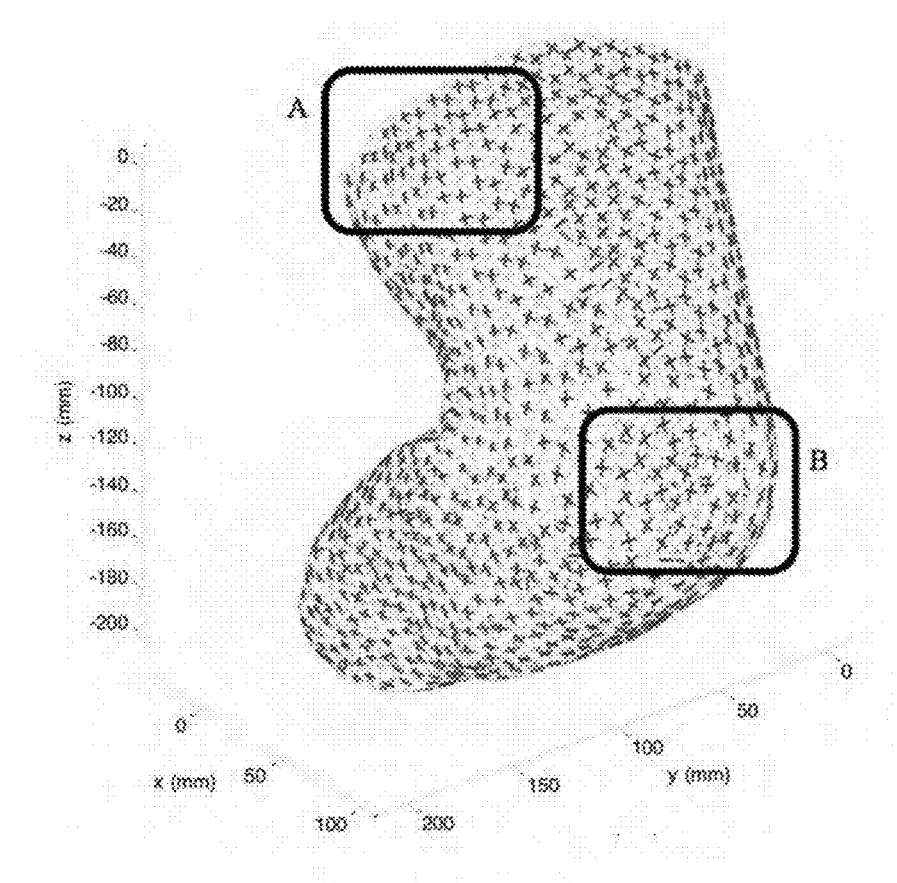
FIG. 6A is a strain field of the knee flexed to approximately 90 degrees.

The strain field can be computed using the information from the SVD of each triangle. FIG. 6A shows a plot of the strain field for the particular case of a transtibial amputation. The red vectors represent the direction and magnitude of the larger of the two normal strains of each triangle. The blue vectors represent the smaller strain. Any shear strain is represented by the angle between the corresponding red and blue vectors of a particular triangular element. The strains throughout each triangle are assume to be constant and are therefore plotted at the centroid of each triangle. If a high enough dot resolution is used, a constant strain element analysis is sufficient to assess the strain state of a deformed surface.

Figures 6B, 6C:
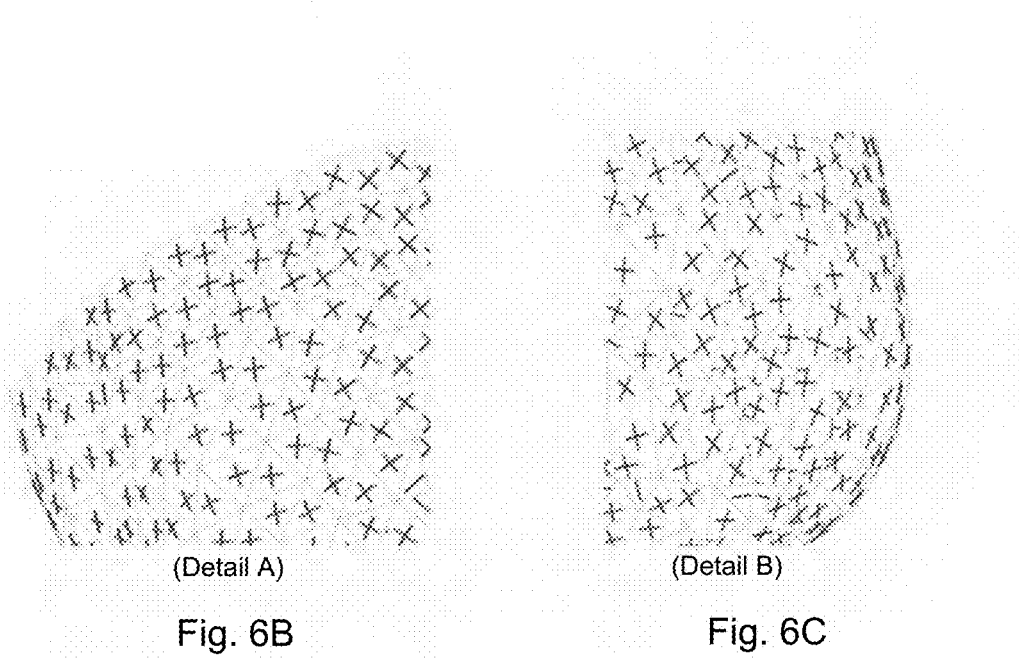
FIG. 6B is the detail A indicated in FIG. 6A.
FIG. 6C is the detail B indicated in FIG. 6A.

More specifically, FIG. 6 shows the strain field of the knee flexed to approximately 90 degrees. It should be noted how the larger (red) strain field is nearly horizontal proximal to the knee joint as the skin stretches circumferentially to accommodate the contractions of the hamstring and quadriceps muscles, as shown in Detail A of FIG. 6B. Further, large strains are highly longitudinal at the knee patella, and just proximal to the patella, as the skin stretches over the patella during knee flexion, as shown in Detail B of FIG. 6C. Here, the longitudinal direction is along the long axis of the femur.

Segment Shape

A critical data set relevant to the design of a mechanical interface is unloaded body shape. Using the photogrammetric data collection procedure outlined in the previous section, the unloaded shape of the biological segment at any given static joint pose can be ascertained simply by fitting a shape model to the coordinate x, y, z data of each skin dot or marking, such as in FIGS. 4A-C. Other non-contact instruments can also be used to measure the shape of a biological segment, using for example imaging tools such as three-dimensional laser scanners, MRI or ultrasound. Alternatively, instruments designed to be in physical contact with the biological body segment of interest can be used to estimate its unloaded shape. Using an instrument with skin contact and position sensing, the x, y, z location of any point on the skin surface can be measured by simply touching the skin lightly at that point. By repeatedly touching the skin surface at a high resolution of skin points, the shape of the limb can ultimately be determined.

Tissue Viscoelastic and Sensitivity Properties

Other critical data relevant to the design of a mechanical interface are tissue viscoelastic and sensitivity properties for orthogonal body compressions. Instruments can be used to estimate the impedance (stiffness and damping) of body tissue through physical contact with the biological body. Here the impedance is measured directly by the instrument by physically applying a force to the body at a single point, or at several points across a region, or through the application of a pressure across a broader region. As force is applied perpendicular to the body's surface at each anatomical point, or node of interest, the instrument's sensors can measure the global three-dimensional location of the body surface point where the force is being applied, the applied tissue deflection, time rate of change of tissue deflection and the applied force or pressure. These measured data can then be used to estimate tissue impedance, or viscoelastic property, of the body segment as a function of anatomical location, thereby establishing a viscoelastic map of the body part or segment.

In addition to these viscoelastic tissue measurements, by way of the instrument's physical contact with the body surface, a direct quantitative measurement of sensitivities to applied force/pressure can be ascertained. For example, relevant to shoe design, the foot-ankle complex may have sensitive areas caused by a bunion deformity, Haglund's deformity or Heel Spur Syndrome all having the potential to lead to the development of painful bursitis. A shoe's design should take into account such sensitivities by using not only a tissue viscoelastic map but also a Sensitivity Map. A sensitivity map comprises the tissue stress/strain threshold at each anatomical point that first results in discomfort for the subject at a maintained stress/strain application. When such an instrument in physical contact with the subject's body exerts a force/pressure at a particular anatomical location, as the applied force/pressure increases, there will be a point when the subject first experiences discomfort at a particular stress or strain level of tissue deformation. A sensitivity map shows this critical level, or threshold, of stress, or strain, as a function of anatomical location. In the design of the mechanical interface, load can then be mitigated from key anatomical areas of sensitivity to reduce internal strains/stresses and wearer discomfort.

Blood Flow and Nerve/Spinal Conduction Dynamics

Imaging tools such as ultrasound can be used to measure blood flow dynamics and nerve/spinal conduction. Such data correlated to anatomical location are critical to the design of a wearable garment or device, since external loads applied to the biological segment from the wearable might alter such dynamics and cause a health problem and/or discomfort for the wearer.

Ultrasound is most useful for observing soft tissue structure within the body. In fact, hard tissue degrades the quality of ultrasound images and impedes the visibility of soft tissue behind/beneath it. Ultrasound is characterized by its sound frequency, ranging between 2-15 MHz, which is much higher than the audible range of humans (20-20,000 Hz) but low enough to not seriously agitate living tissue. It also contains no ionization radiation, making it safer in higher doses than x-ray imaging.

The key component of ultrasound devices is the transducer. It is the piece responsible for sending and receiving sound waves, controlled by the piezoelectric effect. When an electric signal is applied to a crystal within the transducer, it emits a sound at a given frequency. This is the piezoelectric effect. The emitted sound travels through the body and is reflected by tissues. Since the piezoelectric effect is a reversible process, reflected sound waves will yield an electrical signal from the transducer's crystal when they interact with it following reflection. A computer interprets these signals using opacity to symbolize tissue density. A variety of transducers exist with sizes, shapes, and functions that are designed to make them more useful for specific tasks.

Image generation is dictated by the rate at which sound waves are reflected within the body. The speed of sound within the human body is known to be 1540 meters per second, which makes possible the calculation of tissue depth given reflection time (i.e. time of signal return). Max depth and resolution are a function of frequency. Higher frequencies have better resolution but do not penetrate as deeply. Higher frequencies equal higher attenuation. Generally, it is best to choose the highest possible frequency that will achieve the depth of interest. To determine the achievable depth of a specific sound frequency, use the following equation:

$$d_{max} = \frac{v_{sb}}{f} \quad (4)$$

where $d_{max}$ is the maximum achievable depth, $v_{sb}$ is the speed of sound within the human body, and f is the sound frequency. Typical frequencies for deep body imaging range from 1.5 to 3 MHz, while frequencies for superficial structures range from 5 to 10 MHz. Transducers are often characterized by their ability to yield a range of frequencies and must be chosen accordingly.

Biological-Limb Modeling

After the biological limb is captured using photogrammetric tools, the biological limb of interest can be imaged with a MRI machine and/or an electromechanical instrument can be used for measuring biological-limb, viscoelastic and sensitivity properties. Once these additional data are collected, a grid of resolution matched to the skin of the patient (e.g. average 1×1 cm) is established where a node of known variables is created around each grid or averaged for a defined grid. Alternatively, the grid could correspond to the grid of skin-strain triangles, for which FIGS. 6A-C provide an example, where a node is the center point within each respective triangle. Each biological node vector V(i) has properties including, but not limited to, anatomical 3D location with no tissue load, maximal skin tensile strain due to joint movement, orthogonal compression stiffness K and damping B as a function of tissue compression and compression rate, and the sensitivity to externally-applied pressure influenced by blood flow and nerve conduction dynamics, and the presence of chronic tissue wounds such as bursitis. Here the compression stiffness and damping, or impedance, is defined as the biological limb's response to a displacement impulse perpendicular to the skin at each node. Further, the maximum skin tensile strain is computed as the average strain of the three legs of the corresponding strain triangle (See FIG. 5 as an example).

Figure 7A:
FIG. 7A shows a 3D view of bones and patella tendon is shown for the right residual limb of a transtibial amputee.
Figure 7B:
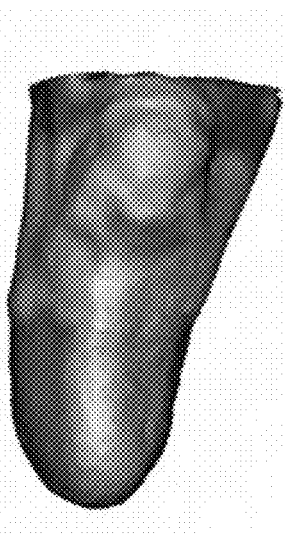
FIG. 7B shows the orthogonal distance D between the unloaded skin surface and a bone intersection.
Figure 7C:
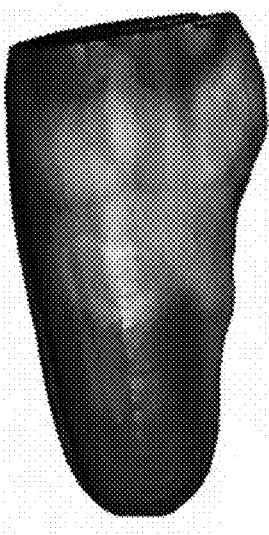
FIG. 7C shows another view of the orthogonal distance D between the unloaded skin surface and a bone intersection.

As an example, FIGS. 7A-C show a simple model of the residual limb of a transtibial amputee generated from MRI data. The model provides the unloaded shape and soft tissue depth of the residual limb as a function of anatomical location. Here soft tissue depth, D, is defined as the perpendicular distance from a node skin surface area and the intersection of that line with a bone. Although tissue depth correlates approximately to body stiffness, K, it is understood that a more sophisticated modeling exercise of soft tissue biomechanics would produce a more precise model of the residual limb's compression stiffness, K, and damping, B, properties as a function of anatomical location and neural activation. Here neural activation is included since large changes in viscoelastic properties occur depending upon whether muscles are activated or relaxed. Such a biological segment model would also include information on the locations of nerve and veins, and their relative pressure tolerances.

In FIG. 7A, a 3D view of bones and patella tendon is shown for the right residual limb of a transtibial amputee. The images in FIGS. 7B and 7C show the orthogonal distance D between the unloaded skin surface and a bone intersection. Here, red regions show large tissue depths, yellow regions moderate depths, and green regions small depths. For these depth models, the patella tendon was removed, exposing the soft tissue depth in the region of the patella tendon just distal to the patella (shown as the red region in the image of FIG. 7B).

Data Acquisition Instruments

Synthetic-Actuated Instruments

Instruments in physical contact with the subject's body comprising synthetic actuator(s) can be used to estimate 1) the orthogonal impedance of body tissue at each anatomical point (viscoelastic map), and 2) the stress or strain tissue threshold where the subject first experiences discomfort at each anatomical point (sensitivity map). Here orthogonal impedance refers to tissue stiffness and damping properties for a tissue state (position and velocity) disturbance directed orthogonal to the surface of the skin at each anatomical location across the body segment of interest.

A viscoelastic map can be ascertained through a three-step process. First, the tissue is measured by sensors where actuators apply a series of controlled interactions that deflect the tissue. Second, the data—position and force with respect to time—is conditioned for system identification purposes. Lastly, the data are used to identify a linear or non-linear transfer function which describes the physical response of the tissue to a given load (force) or deflection.

The collected data consist of positions and forces that are referenced to time. This time reference allows velocity and acceleration to be calculated as well. In order to identify the system, we will look at the input versus the output of the system. Let's say the input is X(t) and the output is Y(t). In order to get an idea of the linear transfer function, we first take the autocorrelation of the input function X(t) to get $X_{ac}(t)$. We then take the cross correlation of the input and output to get $XY_{cc}(t)$. Next a specialized matrix called the Toeplit matrix is formed with $X_{ac}(t)$: TP(t). Then, the impulse response function of the system, h, is $F_s(TP(t)^{-1} \cdot XY_{cc}(t))$. Where $F_s$ is the frequency of the samples and $TP(t)^{-1}$ is the inverted Toeplitz matrix. Given a linear system, the parameters of the transfer function can be determined from the impulse response.

Impedance data can be collected using a ring of linear actuators that surround the biological limb to be mapped.

Such an actuator ring is capable of measuring every point on the ring at the same time. Between 1 and 50 points (or as many as space allows) can be measured simultaneously with this method. Each linear actuator must be independently controlled with its own force and position sensors. A simpler device could be used comprising a single actuator but considerably more time would be required to measure tissue impedance at high resolution across the biological segment of interest.

Human-Actuated Instruments

Alternatively, as will be described herein, a human-actuated probe or probes, can be used to map the anatomical, biomechanical and physiological properties of a body part for which a wearable device is to interface. Another way of measuring the body's orthogonal impedance at each anatomical point is with a location aware instrument that has a force sensitive probe, or force sensitive probes. With such an instrument, a force sensing probe or probes is pushed against the subject's body part of interest where the three-dimensional position of the tip of the probe(s) is measured by the instrument at all times. Additionally, if the body part under measurement is not stationary, the instrument must also track its location in the same three-dimensional reference frame as the measurement probe, or probes. Such a probe, or probes, can be positioned at the surface of the human body in a perpendicular orientation to the surface area of the skin at each anatomical point, and the probe user (practitioner/clinician/user) can then push with varying force, compressing the subject's tissues. Since the force-sensing probe, or probes, measure(s) position, both of itself and of the biological part, both the viscoelastic and sensitivity maps can be ascertained for the body part of interest.

The probe can measure force with a simple spring and linear position measurement device. Through a measurement of the deflection of the sensor's physical spring, the force can be estimated using the force-deflection relation of the spring (e.g. $F=-kx$). The probe could also have a force sensor that is either capacitive, resistive, piezoelectric based, strain-gauge based, or any other force sensing technology. In addition, the probe can also include ultrasound to image the body to ascertain internal tissue properties and blood flow and nervous tissue transduction dynamics, and how such dynamics change as increasing force is applied on the tissue. Ultrasonic transducers on the probe's tip can be used to gather very detailed tissue density data, soft tissue depth (orthogonal distance from the bodies surface to the bone), and blood flow dynamics (e.g. how blood flow is altered upon increasing applied external pressure).

The position sensing system can be physically connected to the probe, such as a structure of linkages similar to that of an industrial robot arm where each linkage has angular position sensors that are capable of determining the exact position of the probe's tip from a grounded reference frame. In addition, the pen could have markers on its surface that could be seen by cameras. Such cameras can be used to triangulate the position of the probe or probes. The probe could also broadcast electromagnetic signals that are picked up by nearby electromagnetic sensors for the purposes of determining the position of the probe. Furthermore, the probe could use a combination of gyroscopes, accelerometers, and magnetometers to aid in determining its position in 3-D space.

The photogrammetric, force, position, velocity, acceleration and ultrasound data from the probe can be communicated wirelessly or wired. The wireless method can be IR-based, Bluetooth, or any other wireless communication method such as an open electromagnetic frequency.

The location of the human body part under measurement can be determined in much the same way as the location of the probe. Using electromagnetic signals, accelerometers, gyroscopes, magnetometers, passive location markers located on the biological limb and external lab frame cameras that measure the locations of these markers, active markers on the biological limb and receivers positioned off the limb in lab frame, or any other location technology or combination of location technologies.

Hybrid-Actuated Instruments

Alternatively, as will be described herein, a third category of instrument comprises both synthetic actuation and human-powered actuation.

In accordance with the present invention, four embodiments will be described that fall within the instrument categories of human-actuated and hybrid-actuated. Each embodiment's design, and its advantages and disadvantages are described herein.

Embodiment I

Single Probe on a Flexible Arm

Figure 8A:
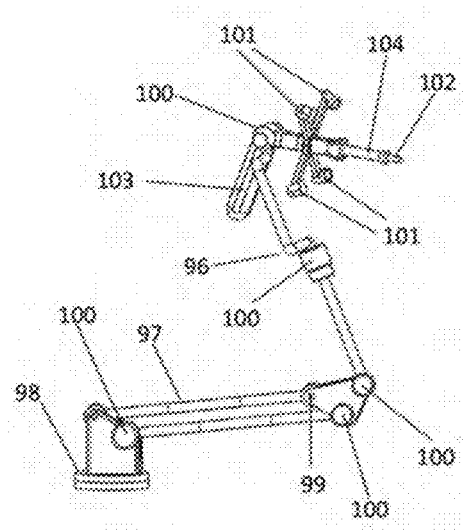
FIGS. 8A and 8B show different views of a single probe on a flexible arm.

A position-aware, force and ultrasound probe can be used to collect anatomical, biomechanical and physiological data describing a biological segment of interest. The single probe embodiment is human-actuated since muscle action from the user of the probe is used to apply probe positions and forces around, and onto, the biological segment. The single probe on a flexible arm is shown in FIG. 8A with a close up view shown in FIG. 8B.

The single probe 96 is attached to a flexible arm 97 from a base 98 attached to a stationary lab frame location. The arm is flexible with rotary joints, e.g. at 99, in order to orient the probe tip to any location within an extensive 3-D volume. Precision encoders 100 are located throughout the flexible arm 97 to allow for real time estimates of the location of the probe tip 102 in 3-D space.

The probe itself comprises photogrammetric, kinetic, and ultrasound sensing. Four small cameras 101 are positioned around the longitudinal axis of the probe. In addition, male probe tip 102 moves linearly into and out of female probe housing 104 when forces are applied to probe tip 102. A compression spring 106 and a linear potentiometer 108 serve as the force sensor within female probe housing 104. When probe tip 102 is pushed onto a biological body segment, compressing its tissue, a force is exerted on force sensor spring 106. Force sensor spring 106 compresses against spring block 107 mechanically grounded to female probe housing 104. The compression of sensor spring 106 is then measured by linear potentiometer 108. Since the stiffness of sensor spring 106 is known, the sensing of spring compression provides force information. The probe also comprises ultrasound. Within probe tip 102, and concentric with its longitudinal axis, is ultrasound probe 105. As probe tip 102 compresses biological tissue, ultrasound probe 105 measures blood flow and tissue properties (soft tissue depth and density) in the local tissue region beneath the probe.

Figure 9:
FIG. 9 shows a single probe on a flexible arm collecting anatomical, biomechanical and physiological data of a transtibial residual limb.

Turning now to FIG. 9, a single probe on a flexible arm is shown for collecting anatomical, biomechanical and physiological data of a transtibial residual limb. FIG. 9 shows the single probe on a flexible arm 96 conducting measurements on a residual limb 109 of a transtibial amputee patient. The following steps are taken to collect a full data set of the residual limb.

Step 1.

In a first step, the skin strain and unloaded shape of the biological segment is measured as a function of joint pose using the procedure outlined previously. To this end, the biological limb is first marked with a matrix of small (~2 mm diameter), black-ink dots 110 across the entire skin-surface area for which the interface is designed to interact. The specific anatomical location and distance between these dots 110 need not be precise, but the resolution, or the number of dots per $cm^2$ is important, as this resolution defines the resolution of the resulting skin strain field. Further, the pattern of dots should be randomized, providing the opportunity to create a unique skin speckle pattern for each anatomical region. As an alternative to a matrix of small dots, the skin of the biological segment of interest can be speckled with a sponge where the sponge is first dipped into FDA approved body paint. By dabbing the painted sponge across the skin surface, a unique pattern of skin speckles can be created.

Step 2.

Next, separate poses, or joint postures of the biological segment of interest, are captured using the four cameras 101 on the single probe. For this step, the user of the probe grabs probe handle 103 and positions the single probe with the cameras 101 pointed towards the biological limb. With the limb held in a static position, the probe user takes a total of ~30 photographs from distinct probe positions, so as to image all sides of the limb. During this exercise, probe tip 102 does not make contact with the biological segment. Using these ~30 digital photographs for each limb pose, 3D models are generated for each limb position. This exercise is then repeated for several limb poses. For example, for the case of the transtibial residual limb shown in FIG. 9, three knee positions could be images: 0, 45 and 90 degrees. As outlined previously, these data are then used to generate both the unloaded shape and skin strain of the biological segment as a function of anatomical location.

Step 3.

Next, the location-aware, force-sensitive probe 96 is used to estimate 1) the orthogonal impedance of body tissue at each anatomical point (viscoelastic map), and 2) the stress or strain tissue threshold where the subject first experiences discomfort at each anatomical point (sensitivity map). Single probe 96 is pushed against the subject's body part (e.g. residual limb 109) where the 3-D position of the probe tip 102 is measured by the instrument at all times using high precision encoders 100 and spring compression potentiometer 108. Additionally, if the body part under measurement is not stationary, the single probe 96 also tracks its location in the same 3-D reference frame as the measurement probe. The probe tip 102 is positioned at the surface of the human body in a perpendicular orientation to the surface area of the skin at each anatomical point, and the probe user (practitioner/clinician/user) then pushes with varying force, compressing the subject's tissues. Since the force-sensing probe measures position, both of itself and of the biological part, both the viscoelastic and sensitivity maps are ascertained for the body part of interest.

The anatomical locations where tissue impedance and sensitivities are measured can be at each dot of the speckled pattern (e.g. 110 in FIG. 9). In so doing, impedance/sensitivity measurements at all three vertices of each triangular element (e.g. in FIG. 5) can be determined. In so doing, tissue orthogonal stiffness, damping and stress/strain level where discomfort occurs can be correlated with the x, y, and z of each triangular node, where the peak skin strain is also known between all node points.

Since the pattern of skin speckles 110 is unique at each anatomical location, a single camera image from cameras 101 taken of a small region of the skin surface can be used to determine the anatomical position at which the camera's lens is pointed or directed. Since the geometric position of each camera is fixed relative to probe tip 102 and ultrasound probe 105 with knowledge of probe spring 106 compression, the anatomical location of probe tip force application on the body can be determined. As noted previously, such an anatomical-positioning algorithm is achieved by comparing the single, anatomically-local image to the full speckle patterns across the entire biological segment determined in Step 2. With such a positioning algorithm, the biological limb can move during the times when impedance measurements are not being made without having to measure such limb movements. However, during an impedance measurement the biological limb has to remain stationary globally, or if there is translational or rotational limb bone movement, such movements have to be measured, so as to determine accurately the amount of tissue compression caused by the probe force. Here the translation of the biological limb bone structure along the longitudinal axis of the probe has to be subtracted from the measured probe tip 3-D location upon tissue force application to determine an accurate measure of tissue compression and ultimately tissue impedance.

In addition, probe 96 uses ultrasound 105 to image the body to ascertain internal tissue properties and blood flow and nervous tissue transduction dynamics, and how such dynamics change as increasing force is applied on the tissue by probe tip 102. Ultrasound transducer 105 within probe tip 102 is used to gather very detailed tissue density data, soft tissue depth (orthogonal distance from the bodies surface to the bone), and blood flow dynamics. Since single probe 96 measures force simultaneous with the ultrasound measurement, blood flow just beneath the ultrasound probe 105 can be measured as a function of applied probe force to determine how blood dynamics may be altered upon increasing applied external pressure.

Finally, the stress or strain tissue threshold where the subject first experiences discomfort at each anatomical point is measured to produce a sensitivity map. Here the subject verbally reports his/her level of discomfort with each applied probe force for each anatomical point at which probe force is applied. When the subject first reports discomfort at each anatomical location, that applied force and tissue strain is recorded and later used to create a sensitivity map.

Embodiment II

Probe Array on a Flexible Arm

To increase the speed with which the body part of interest can be anatomically, biomechanically and physiologically mapped, multiple probes can be employed. This embodiment represents a human-actuated instrument where the instrument's user, under their own muscle control, applies positions about, and forces onto, the biological segment of interest. In FIG. 10A, a probe array 115 is shown on a flexible arm 119. A close up of the probe array 115 is shown in FIG. 10B. In this embodiment, a plurality of male probes 116 move linearly into and out of a probe head 117. Inside probe head 117 are force sensors for measuring the force applied on each male probe 125 when each male probe 125 is pushed against a biological segment, compressing tissue and applying force. In addition to force, each male probe 125 has an ultrasound probe 126 mounted co-axially inside the tip of the male probe 125. In addition, a small camera 127 is mounted on the outside surface, or diameter, of each male probe 125.

Flexible arm 119 comprises rotary joints (e.g. 121) so that each male probe 125 can be positioned anywhere in a large 3-D volume relative to flexible arm base 120. To accurately measure the 3-D position of the tip of each male probe 125, high precision encoders 122 contribute to the precise measurement of the lab frame position of each male probe 125.

A practitioner/clinician/subject grabs handle 118 of the probe array and pushes the probe array against a body surface of interest where the probes are approximately perpendicular to the body's surface. An example is shown in FIG. 11 where two probe arrays 130, 131 are pressed against the residual limb of a transtibial amputee 132. As shown, each probe array (right 130 and left hand 131) are co-axially aligned; for example, in the configuration shown in FIG. 11, the longitudinal axis of each individual probe 125 of the right hand probe array 130 is co-axially aligned with its corresponding individual probe within the left hand probe array 131. Through this co-axial alignment between the two opposing probe arrays, the forces applied on the body segment sum to zero since the user of the probe arrays (clinician/practitioner/subject) exerts equal and opposite forces where all probe forces sum to zero. With the net external force applied equal to zero, the biological limb's effective center of mass remains stationary, where the internal bones of the limb do not accelerate when the limb's external tissues are being compressed by the probe arrays. If the user of the probe array is careful to balance applied forces from the array onto the biological limb, the limb will not translate and thus, measuring the position and orientation of the biological limb (e.g. 132) may not be necessary. If there is a risk that the biological limb will translate and/or rotate during tissue-compression experiments, technologies can be used to measure the limb's full orientation in 3-D space. For example, passive reflective markers can be positioned on the biological limb, and the individual probe cameras 127 can measure the x, y, z locations of these markers relative to lab frame in 3-D space. If during tissue compression the biological limb moves, this movement can be subtracted away from the x, y, z location of each probe's tip or point of tissue contact when estimating the amount of tissue compression, and the speed of tissue compression. Other technologies can be used to determine the position of the biological limb during probe measurements including, but not limited to, electromagnetic signals, accelerometers, gyroscopes, magnetometers, active markers on the biological limb and receivers positioned off the limb in lab frame, or any other location technology or combination of location technologies.

Still referring to FIG. 11, two probe arrays 130 and 131 are shown on each on flexible arms used in the mapping of a residual limb 132 of a transtibial amputee patient. The following steps are taken to collect a full data set of a biological limb segment.

Step 1.

In a first step, the skin strain and unloaded shape of the biological segment is measured as a function of joint pose using the procedure outlined previously. To this end, the biological limb is first marked with a matrix of small (~2 mm diameter), black-ink dots across the entire skin-surface area for which the interface is designed to interact. The specific anatomical location and distance between these dots need not be precise, but the resolution, or the number of dots per cm² is important, as this resolution defines the resolution of the resulting skin strain field. Further, the pattern of dots should be randomized, providing the opportunity to create a unique skin speckle pattern for each anatomical region. As an alternative to a matrix of small dots, the skin of the biological segment of interest can be speckled with a sponge where the sponge is first dipped in FDA approved body paint. By dabbing the painted sponge across the skin surface, a unique pattern of skin speckles can be created.

Step 2.

Next, separate poses, or joint postures of the biological segment of interest, are captured using the cameras 127 on each probe. For this step, the user of the probe array grabs probe handle 118 and positions the probe array with cameras 127 pointed towards the biological limb. With the limb held in a static position, the probe array user takes a total of ~30 photographs from distinct probe positions, so as to image all sides of the limb. During this exercise, the tip of probe 125 does not make contact with the biological segment. Using these ~30 digital photographs for each limb pose, 3D models are generated for each limb posture. This exercise is then repeated for several limb poses. For example, for the case of the transtibial residual limb shown in FIG. 11, three knee positions could be images: 0, 45 and 90 degrees. As outlined previously, these data are then used to generate both the unloaded shape and skin strain of the biological segment as a function of anatomical location.

Step 3.

Next, the location-aware, force-sensitive probe array 115 is used to estimate 1) the orthogonal impedance of body tissue at each anatomical point (viscoelastic map), and 2) the stress or strain tissue threshold where the subject first experiences discomfort at each anatomical point (sensitivity map). Probe array 115 is pushed against the subject's body part (e.g. residual limb 132) where the 3-D position of the tip of each male probe 125 is measured by the instrument at all times using high precision encoders 122, and the spring compression potentiometer corresponding to said male probe 125 housed within probe head 117. Additionally, if the body part under measurement is not stationary, the probe array 115 also tracks its location in the same 3-D reference frame as the measurement probe array. The tip of each male probe 125 is positioned at the surface of the human body in a perpendicular orientation to the surface area of the skin at each anatomical point, and the probe array user (practitioner/clinician/subject) then pushes with varying force, compressing the subject's tissues. Since the force-sensing probe array measures position, both of each individual male probe 125 and of the biological part (e.g. 132), both the viscoelastic and sensitivity maps are ascertained for the body part of interest.

Since the pattern of skin speckles 110 (Step 1) is unique at each anatomical location, a single camera image from each camera 127 taken of a small region of the skin surface can be used to determine the anatomical position at which the camera's lens is pointed or directed. Since the geometric position of each camera is fixed relative to the tip of each male probe 125 and ultrasound probe 126 with knowledge of each male probe's relative compression distance within probe head 117, the anatomical location of the application of each male probe tip on the body can be determined. As noted previously, such an anatomical-positioning algorithm is achieved by comparing the single, anatomically-local image to the full speckle patterns across the entire biological segment determined in Step 2. With such a positioning algorithm, the biological limb can move during the times when impedance measurements are not being made without having to measure such limb movements. However, during an impedance measurement the biological limb has to remain stationary globally, or if there is translational or rotational limb bone movement, such movements have to be measured, so as to determine accurately the amount of tissue compression caused by each male probe 125 force. Here the translation of the biological limb bone structure along the longitudinal axis of each male probe 125 has to be subtracted from the measured male probe 125 displacement upon tissue force application to determine an accurate measure of tissue impedance.

In addition, probe array 115 uses ultrasound 126 to image the body to ascertain internal tissue properties and blood flow and nervous tissue transduction dynamics, and how such dynamics change as increasing force is applied on the tissue by the tip of each male probe 125. Ultrasound transducer 126 within each male probe tip 125 is used to gather very detailed tissue density data, soft tissue depth (orthogonal distance from the bodies surface to the bone), and blood flow dynamics. Since probe array 115 measures force applied to each male probe simultaneous with the ultrasound measurement, blood flow just beneath each ultrasound probe 126 can be measured as a function of applied probe force to determine how blood dynamics may be altered upon increasing applied external force via each male probe 125.

Finally, the stress or strain tissue threshold where the subject first experiences discomfort at each anatomical point is measured to produce a sensitivity map. Here the subject verbally reports his/her level of discomfort with each applied probe force for each anatomical point at which probe force is applied. When the subject first reports discomfort at each anatomical location, that applied force and tissue strain is recorded and later used to create a sensitivity map.

Although the probe array 115 can map a biological limb faster than the single probe of embodiment I, it has several disadvantages. First, since the probe array is planar where each probe tip is the same length at equilibrium when no force is applied, each probe would not apply a force that is perpendicular to the bodies' surface, especially when the biological body's surface is highly curved. Second, a sensitivity map is difficult to measure since reported discomfort by the subject cannot be precisely attributed to an exact anatomical location or to a specific male probe 125.

Embodiment III

Finger Probe on a Flexible Arm

Figure 12A:
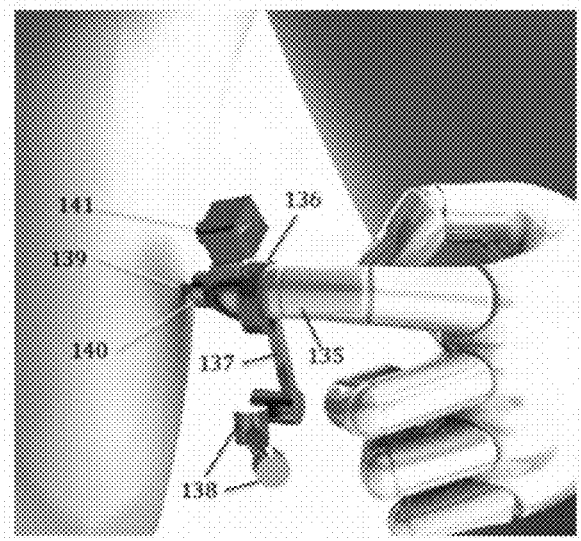
FIGS. 12A and 12B different views of a finger probe on a flexible arm.
Figure 12B:
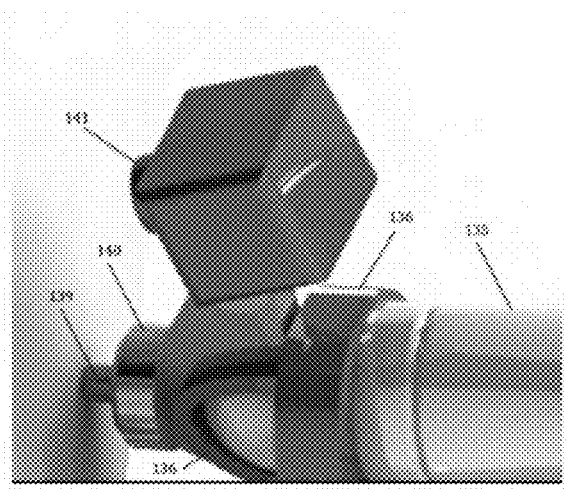

Embodiment III overcomes Embodiment II's lack of probe orthogonality and location specificity, while improving Embodiment I's speed with which a biological segment can be mapped anatomically, biomechanically and physiologically. This embodiment represents a human-actuated instrument where the instrument's user, under their own muscle control, applies positions about, and forces onto, the biological segment of interest. In FIGS. 12A and 12B, a finger probe on a flexible arm is shown. Finger 135 inserts into finger socket 136 that is connected to a flexible arm 137 with high precision encoders 138 at each arm degree of freedom to determine the global 3-D position in space of finger socket 136. Mounted on finger socket 136 is male probe 139 that moves linearly into, and out of, female probe housing 140. When male probe 139 compresses tissue, it pushes on a force sensor within the female probe housing 140.

Figure 8B:
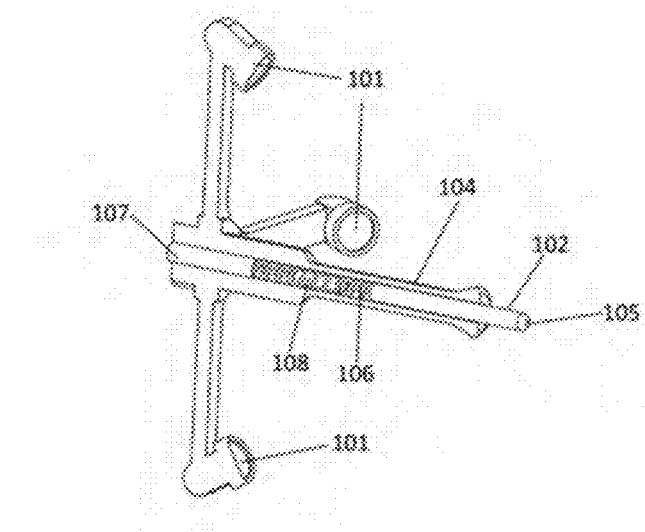

The force sensor comprises a spring and linear potentiometer such as described in Embodiment I, as best seen in FIG. 8B; spring 106 and potentiometer 108). The probe measures force with a simple spring and linear position measurement device. Through a measurement of the deflection of the sensor's physical spring housed in the female probe housing 140, the force can be estimated using the force-deflection relation of the spring (e.g. $F=-kx$). It will be understood by those of ordinary skill in the art that the finger probe could also have a force sensor that is either capacitive, strain-gauge based, or resistive. In addition, the finger probe also includes ultrasound to image the body to ascertain internal tissue properties and blood flow and nervous tissue transduction dynamics, and how such dynamics change as increasing force is applied on the tissue. An ultrasonic transducer probe is co-axial with male probe 139 and is used to gather very detailed tissue density data, soft tissue depth (orthogonal distance from the bodies surface to the bone), and blood flow dynamics (e.g. how blood flow is altered upon increasing applied external pressure). For photogrammetric data, a small camera 141 mounts on finger socket 136.

Figure 13:
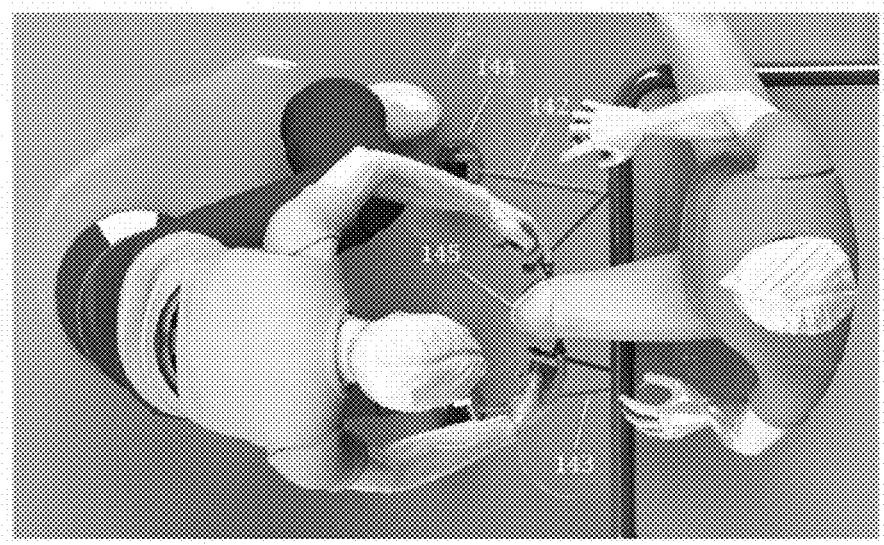
FIG. 13 shows finger probes on flexible arms collecting anatomical, biomechanical and physiological data of a transtibial residual limb.

FIG. 13 shows finger probes on flexible arms collecting anatomical, biomechanical and physiological data of a transtibial residual limb. Two finger probes, one for the left hand 142 and one for the right hand 143 are preferably provided. Each probe is attached to a lab frame location through a flexible arm base 144.

A known geometric relationship exists between the mounting location of camera 141 on finger socket 136 and the location of female probe housing 140. Given the measured amount of insertion of male probe 139 into female housing 140, or probe force via the potentiometer recording, the precise location of the tip of the male probe 139 to finger socket 136 and camera 141 is known and can be recorded with a data acquisition system. Further, via position sensing from precision encoders 138, the location of the finger socket 136 is known relative to flexible arm base 144 of flexible arm 137 and can likewise be recorded with a data acquisition system.

It should be understood by those of ordinary skill in the art that communication wires from the finger probe force sensor, camera, ultrasound probe and encoders can travel through flexible arm 137 or adjacent the arm. Alternatively, an antenna can be positioned on the finger socket 136 for wireless transmission of sensory data to a receiver within a data acquisition system comprising computer, A/D conversion, signal conditioners, and power supply. Specifically, the photogrammetric, force, position, velocity, acceleration and ultrasound data from the finger probe can be communicated wirelessly or wired. The wireless method can be IR-based, Bluetooth, or any other wireless communication method such as an open electromagnetic frequency.

FIG. 13 shows two finger probes 142 and 143 each on flexible arms used in the mapping of a residual limb 145 of a transtibial amputee patient. The following steps are taken to collect a full data set of a biological limb segment:

Step 1

In a first step, as with Embodiments I and II, the skin strain and unloaded shape of the biological segment is measured as a function of joint pose. To this end, the biological limb is first marked with a matrix of small (~2 mm diameter), black-ink dots across the entire skin-surface area for which the interface is designed to interact. The specific anatomical location and distance between these dots need not be precise, but the resolution, or the number of dots per $cm^2$ is important, as this resolution defines the resolution of the resulting skin strain field. Further, the pattern of dots is randomized, providing a unique skin speckle pattern for each anatomical region. As an alternative to a matrix of small dots, the skin of the biological segment of interest can be speckled with a sponge where the sponge is first dipped into FDA approved body paint. By dabbing the painted sponge across the skin surface, a unique pattern of skin speckles 110 can be created.

Step 2

Next, separate poses, or joint postures of the biological segment of interest, are captured using the camera 141 on each finger probe. For this step, the user of the finger probe positions the finger probe with camera 141 pointed towards the biological limb. With the limb held in a static position, the finger probe user takes a total of ~30 photographs from distinct finger probe positions, so as to image all sides of the biological limb. During this exercise, the tip of male probe 139 does not make contact with the biological segment. Using these digital photographs for each limb pose, 3D models are generated for each limb posture or pose. This exercise is then repeated for several limb poses. For example, for the case of the transtibial residual limb shown in FIG. 13, three knee positions could be images: 0, 45 and 90 degrees. As outlined previously, these data are then used to generate both the unloaded shape and skin strain of the biological segment as a function of anatomical location.

Step 3

Next, the location-aware, force-sensitive finger probe is used to estimate 1) the orthogonal impedance of body tissue at each anatomical point (viscoelastic map), and 2) the stress or strain tissue threshold where the subject first experiences discomfort at each anatomical point (sensitivity map). Finger probe is pushed against the subject's body part (e.g. residual limb 145) where the 3-D position of the tip of each male probe 139 is measured by the instrument at all times using both the force sensor potentiometer and the high precision encoders 138. Additionally, if the body part under measurement is not stationary, the finger probe also tracks its location in the same 3-D reference frame as the flexible arm base 144. The tip of each male probe 139 is positioned at the surface of the human body in a perpendicular orientation to the surface area of the skin at each anatomical point, and the probe array user (practitioner/clinician/subject) then pushes with varying force, compressing the subject's tissues. Since the force-sensing finger probe measures position, both of the tip of the male probe 139 and of the biological part (e.g. 145), both the viscoelastic and sensitivity maps are ascertained for the body part of interest.

Since the pattern of skin speckles (Step 1) is unique at each anatomical location across the biological segment, a single camera image from mounted camera 141 taken of a small region of the skin surface can be used to determine the anatomical position at which the camera's lens is pointed or directed. Since the geometric position of the camera 141 is fixed relative to the tip of male probe 139 (and corresponding ultrasound probe) with knowledge of male probe's relative compression distance within the female probe housing 140, the anatomical location of the application of each male probe tip on the body can be determined. As noted previously, such an anatomical-positioning algorithm is achieved by comparing the single, anatomically-local image to the full speckle patterns across the entire biological segment determined in Step 2. With such a positioning algorithm, the biological limb can move during the times when impedance measurements are not being made without having to measure such limb movements. However, during an impedance measurement the biological limb has to remain stationary globally, or if there is translational or rotational limb bone movement, such movements have to be measured, so as to determine accurately the amount of tissue compression caused by the male probe 139 force. Here the translation of the biological limb bone structure along the longitudinal axis of the male probe 139 has to be subtracted from the measured male probe 139 global, lab frame displacement upon tissue force application to determine an accurate measure of tissue impedance.

In addition, the finger probe of Embodiment III uses ultrasound to image the body to ascertain internal tissue properties and blood flow and nervous tissue transduction dynamics, and how such dynamics change as increasing force is applied on the tissue by the tip of each male probe 139. The ultrasound transducer within the tip of male probe 139 is used to gather very detailed tissue density data, soft tissue depth (orthogonal distance from the bodies surface to the bone), and blood flow dynamics. Since the finger probe measures force applied to the male probe 139 simultaneous with the ultrasound measurement, blood flow just beneath each ultrasound probe, along the projection of longitudinal axis of male probe 139 into the biological segment, can be measured as a function of applied finger probe force to determine how blood dynamics may be altered upon increasing applied external force.

Finally, the stress or strain tissue threshold where the subject first experiences discomfort at each anatomical point is measured to produce a sensitivity map. Here the subject verbally reports his/her level of discomfort with each applied probe force for each anatomical point at which probe force is applied. When the subject first reports discomfort at each anatomical location, that applied force and tissue strain is recorded and later used to create a sensitivity map.

In increase the speed with which a biological segment can be mapped, many finger probes can be employed up to 10 finger probes, one for each finger on the right and left hands of the finger probe user. A plurality of finger probes can map a biological limb faster than the single probe of embodiment I, without the disadvantages of Embodiment II, namely poor orthogonality and specificity. Since each finger probe is controlled by a biologically-actuated finger, orthogonality can be achieved where each finger probe applies a force perpendicular the body's surface. In addition, since each biological finger is independent in its force application and position, the stress/strain threshold where a subject experiences discomfort at a specific anatomical location can be determined.

Other advantages of the finger probe include its spatial versatility and proximity to the biological segment. Since the finger probe has sensors located directly on each finger tip, it has great spatial versatility; difficult areas of the body can be mapped where there is little space for a bulky instrument. For example, if the upper thigh needs to be mapped in the case of a transfemoral prosthetic socket or leg exoskeleton, the finger probe can readily take measurements in the medial crotch area. The finger probe also has an improved proximity to the biological member compared to other types of instruments such as Embodiment I and II. Since the force, ultrasound, and photogrammetric sensors are located on the biological finger tip, the distance from the fingers to the biological segment being mapped is relatively small, allowing the user of the instrument to more readily palpate the biological member during data collection.

Embodiment IV

Untethered Finger Probe

The spatial versatility of Embodiment III is improved over Embodiments I and II, but the design is still not optimal. Because each finger socket is tethered to a flexible arm in Embodiment III, versatility may be limited since the flexible arm may cause obstructions when mapping some difficult-to-reach body segments. Further, the flexible arm makes the instruments of Embodiment I, II, and III somewhat bulky and difficult to transport.

Figure 14A:
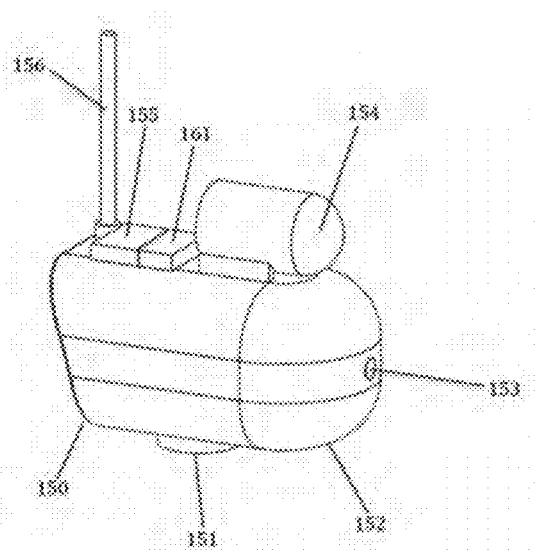
FIG. 14A shows an untethered finger probe.
Figure 14B:
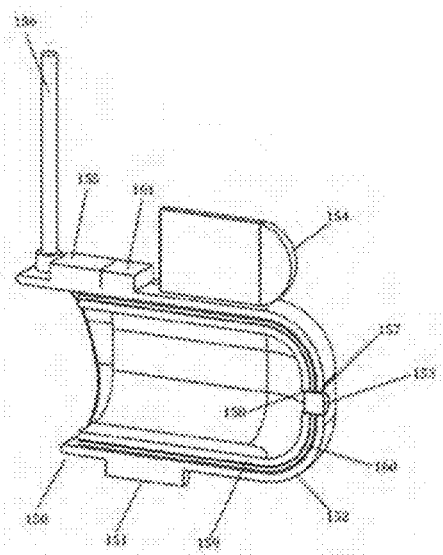
FIG. 14B shows a cross-sectional view of the finger probe of FIG. 14A.

As a resolution to these difficulties, an untethered finger probe is shown in FIGS. 14A and 14B. This embodiment represents a hybrid-actuated instrument comprising both synthetic actuation and human-powered actuation. The probe 150 comprises a hemispherical external finger cap 152 and a hemispherical internal finger cap 159. The external and internal caps, 152 and 159, respectively, are hemispherical at their terminus end, or tip, because: 1) a hemispherical tissue indenter can be readily modeled using finite element modeling software, and 2) when the body is touched lightly by the external cap 152, it interfaces the body with a small surface area or point, making the determination of the contact point more tractable.

The external 152 and internal 159 finger caps are separated by a dielectric elastomer device, or force sensor, 160. While dielectric elastomers have often been used for actuation and power generation, they can also be used as an integrated force sensor. When a dielectric elastomer device (dielectric elastomer material, such as silicone, with imbedded compliant electrodes) is mechanically deformed, both the capacitance and dielectric resistance of the material is changed. Thus, compliant electrodes will be embedded within the dielectric elastomer device 160 to measure mechanical forces applied to the external finger cap 152 when a subject's tissues are being compressed. Relative to the X, Y, and Z coordinate frame of the external finger cap 152, a force vector can be measured having force components in the X, Y, and Z directions. Here Z is perpendicular to the external finger cap outwardly directed along the longitudinal axis of the untethered finger probe 150, and X and Y are orthogonal to this longitudinal Z axis. Specifically, as an example, when a force is applied to external finger cap 152 having a general direction along the longitudinal Z axis of the finger probe 150, the dielectric elastomer device 160 compresses, becoming thinner and undergoing a capacitance change that correlates with an applied Z force. Alternatively, the untethered finger probe 150 could exert a shear force against a biological segment, resulting in a shear force applied to the external finger cap 152, or a force in the XY plane. Such a shear force would cause the dielectric elastomer device 160 to compress with a distinct strain field compared to the strain field caused by the pure Z-axis force of the previous example. Electrode patterning upon the dielectric material of device 160 using microfabrication is designed to differentiate between forces applied in X, Y and Z directions. Such a force sensor 160 offers several potential advantages over traditional sensors including operation over large strain ranges, ease of patterning for distinctive sensing capabilities, flexibility to allow unique integration into components, stable performance over a wide temperature range, and low power consumption.

The dielectric elastomer device 160 comprises silicone positioned between patterned electrodes, one patterning near the inner surface of the layer 160 (in close proximity to the internal finger cap 159), and a second patterning on its outer surface (in close proximity to the external finger cap 152). Such a dielectric sensor measures changes in capacitance when the silicone material is compressed under an externally applied pressure, or force, applied to external finger cap 152. Within the walls of layer 160, conductive traces pass from each electrode to processing unit 155 via external finger cap 152 (not shown). Without loss of generality, finger probe 150 could also have a force sensor that is resistive, piezoelectric based, strain-gauge based, spring-potentiometer based, or any other force sensing technology.

The untethered finger probe 150 also includes ultrasound to image the body to ascertain internal tissue properties, blood flow and nervous tissue transduction dynamics, and how such dynamics change as increasing force is applied on the tissue by external finger cap 152. An ultrasound transducer probe 153 is used to gather very detailed tissue density data, soft tissue depth (orthogonal distance from the bodies surface to the bone), and blood flow dynamics (e.g. how blood flow is altered upon increasing applied external tissue pressure). Ultrasound probe 153 is mechanically grounded to hemispherical external finger cap 152. When a force is exerted on the external finger cap 152, ultrasound probe 153 moves through a clearance hole 158 within the internal finger cap 159. Within the walls of the external finger cap 152, wires pass from the ultrasound probe 153 to processing unit 155 (wiring not shown).

The untethered finger probe 150 also comprises a small camera 154 for the collection of photogrammetric data. Camera wires pass from camera 154 to processing unit 155 (wiring not shown).

Untethered finger probe 150 also comprises a full inertial measurement unit (IMU) 161. The IMU is attached to external finger cap 152, and comprises 3 accelerometers, 3 rate gyros and a magnetometer.

Processing unit 155 includes, but is not limited to, a microprocessor, RAM, A/D conversion, USB port, and power supply. Data from the force sensor 160, ultrasound probe 153, camera 154, and IMU 161 are transmitted to processing unit 155 where basic signal conditioning is performed such as A/D conversion, filtering, amplification, etc. prior to wireless transmission. In one embodiment, during data collection processed sensory data are wirelessly transmitted via antenna 156 to a receiver located on a data acquisition station not attached to the finger probe, but in the vicinity of the probe. It will be understood by those of ordinary skill in the art that the photogrammetric, force, position, velocity, acceleration and ultrasound data from the finger probe can be communicated wirelessly using IR-based, Bluetooth, or any other wireless communication method such as an open electromagnetic frequency. In another embodiment, sensory data are stored on processing unit 155, and later transferred via the USB port to a computer for processing and modeling. In this framework, processing unit 155 has substantial memory for data storage, so that wireless or wired transfer of data could be completed when it is convenient to do so. In a preferred embodiment, memory storage is sufficient to store all the data for at least a complete map of an entire body segment anatomically, biomechanically and physiologically. With such storage space, the transfer of data can occur subsequent to the data collection on the human subject, enabling a greater degree of convenience. This type of framework is critical for data collections that occur in very remote regions of the world, where the transport of a computer is inconvenient. In this type of situation, the untethered finger probe, or probes, could be carried in a backpack to any remote village in poor areas of the world. Subjects could be mapped, and the data set could later be uploaded from the finger probe, or probes, for analysis and design of a mechanical interface.

Finally, untethered finger probe 150 comprises an actuator controlled and powered by processing unit 155. A vibration actuator 151, such as a pager motor, is mechanically grounded to the external finger cap 152. When the vibration actuator is activated, its motor spins an asymmetric mass that causes the finger probe 150 to vibrate. When finger probe 150 is in contact with a biological segment, these vibrations cause a force ripple against the tissue directly beneath the external cap's tissue force application (center of pressure point on external cap 152 due to tissue contact). The dielectric elastomer device 160 and processing unit 155 records such force ripples, and the IMU 161 and processing unit 155 records the accelerations caused by the vibrations. The acceleration data are then low pass filtered by processing unit 155 to estimate the maximum tissue compression and time rate of change of compression. During tissue palpation, the measured force signal from force sensor 160 is combined with the tissue compression, and rate of compression data, to estimate viscoelastic tissue properties directly at the point of application, or center of pressure, between finger probe 150 and the subject's tissue.

Figure 15A:
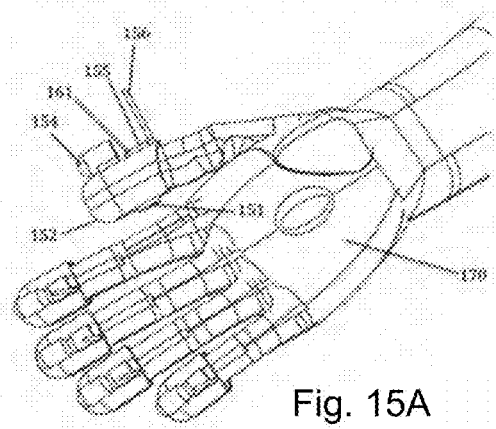
FIGS. 15A and 15B show different views of multiple untethered finger probes.
Figure 15B:
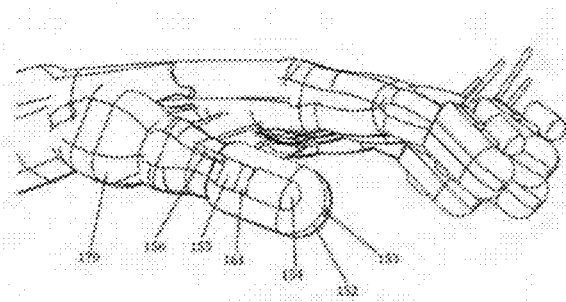

To increase the speed with which a biological segment can be mapped, multiple untethered finger probes can be employed. FIGS. 15A and 15B show different views of five untethered finger probes on each digit of the hand in the form of a data acquisition glove 170. Each finger probe comprises all the elements shown in FIG. 14 including vibratory actuator 151, external finger cap 152, ultrasound probe 153, camera 154, processing unit 155, antenna 156 and IMU 161. It will be understood by those of ordinary skill in the art that a single, central processor and antenna, located on the back of the hand or palm, could be used instead of individual processor units 155 and antenna's 156 on each finger tip. For the case where the computation and wireless transmission hardware were located on the back of the hand, electrical transmission wires would run down the fingers from each individual finger probe 150 to the central processor and antenna.

Figure 16A:
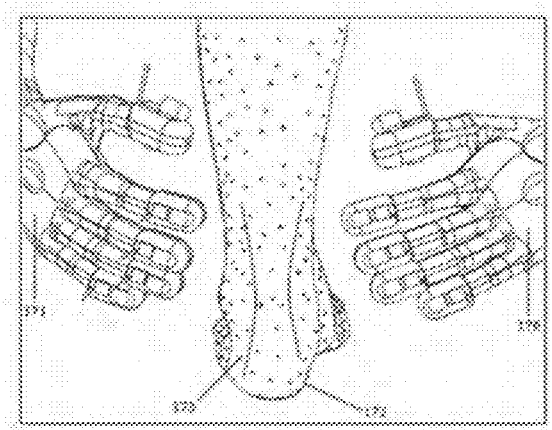
FIGS. 16A and 16B show multiple untethered finger probes collecting anatomical, biomechanical and physiological data of the ankle-foot complex.
Figure 16B:
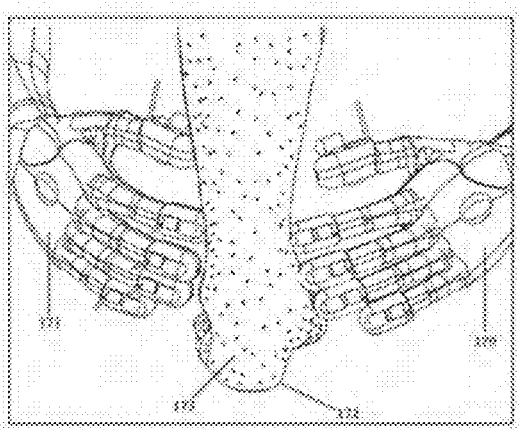

FIGS. 16A and 16B show different view of ten untethered finger probes worn on the left and right hand in the form of two gloves, one for the left hand 170 and a second for the right hand 171. As an example, the ten untethered finger probes in FIG. 16 are used to rapidly map a biological ankle-foot complex 172 that has been speckled 173 with FDA approved body paint. The following steps are taken to collect a full data set of any biological limb segment, including for example the ankle-foot complex shown in FIGS. 16A and 16B.

Step 1

In a first step, as with Embodiments I, II and III, the skin strain and unloaded shape of the biological segment is measured as a function of joint pose. To this end, the biological limb is first marked with a matrix of small (~2 mm diameter), black-ink dots across the entire skin-surface area for which the interface is designed to interact. The specific anatomical location and distance between these dots need not be precise, but the resolution, or the number of dots per $cm^2$ is important, as this resolution defines the resolution of the resulting skin strain field. Further, the pattern of dots is randomized, providing a unique skin speckle pattern for each anatomical region. As an alternative to a matrix of small dots, the skin of the biological segment of interest can be speckled with a sponge where the sponge is first dipped into FDA approved body paint. By dabbing the painted sponge across the skin surface, a unique pattern of skin speckles can be created.

Step 2

Next, separate poses, or joint postures of the biological segment of interest, are captured using the camera 154 on each untethered finger probe. For this step, the user of the untethered finger probes position the finger probes with cameras 154 pointed generally towards the biological limb. With the limb held in a static position, the finger probes' user, or probe operator, takes photographs from distinct finger probe positions, so as to image all sides of the biological segment (~30 or more photographs for each limb pose). To improve image quality, a light flash can be used with each camera 154, and/or a continuous light output source from each camera, so as to minimize problematic shadows that complicate subsequent data processing. During this exercise, the untethered finger probes do not make contact with the biological segment (e.g. Left image in FIG. 16). Using these digital photographs for each limb pose, 3D models are generated for each limb posture or pose. This exercise is then repeated for several limb poses. For example, for the case of the ankle-foot complex shown in FIG. 16, three ankle positions could be imaged: 0 degrees, dorsiflexion 15 degrees and plantar flexion 20 degrees, as well as three subtalar joint positions: 0 degrees, inversion 10 degrees, and eversion 10 degrees. As outlined previously, these data are then used to generate both the unloaded shape and skin strain of the biological segment for each segment pose as a function of anatomical location.

Using the untethered finger probe 150, an alternate method for measuring the unloaded shape of a biological segment is through the use of the IMU 161 and force sensor 160 on each finger probe 150. In this method, the operator of the finger probe 150 starts from a single point marked on the skin in the region of the biological segment of interest. The finger probe operator then moves his finger gently along the surface of the biological segment, with the hemispherical external cap 152 lightly touching the skin surface. During this movement, a position trajectory is computed along those skin points contacted by the external finger cap 152. Specifically, in this method the IMU 161 is used first to estimate the lab frame spatial trajectory (X, Y, Z positions versus time) of the IMU 161 located on the finger probe 150 by performing a zero velocity update when the finger probe is held stationary (zero acceleration except for gravity) at the starting point marked on the skin, and then integrating forward. By integrating forward, the lab frame X, Y, Z IMU trajectory in 3-D space relative to the starting point is computed.

After this IMU trajectory calculation is performed, the estimate of the lab frame X, Y, Z trajectory of the external finger cap contact point against the skin, or center of pressure, is computed by conducting a geometric transformation from the lab frame IMU X, Y, Z trajectory to the measured center of pressure location on the external finger cap 152. In this calculation, the center of pressure position relative to the fixed position of the IMU 161 on the finger probe 150 is computed using the force sensor 160 and the fixed position of the IMU relative to the external cap 152. This local frame position trajectory of the center of pressure point relative to the IMU is then added to the lab frame trajectory of the IMU 161, to compute the lab frame trajectory of the center of pressure point as the finger probe 150 is moved across the skin surface. By repeating this finger movement pattern at a high resolution of skin points, always starting from the same starting point, the shape of the limb can ultimately be determined. To minimize integration drift error from the IMU calculation, the operator's finger movement along the skin surface is done quickly at high velocity starting from a zero-velocity starting point on the skin surface.

It will be understood by those of ordinary skill in the art that many finger movement patterns could be employed to map the shape of a biological limb. For example, the operator could first move his finger to key anatomical points, and then subsequently map the shape of the skin surface relative to these anatomical locations. If for example, there were N anatomical locations geometrically distributed across the biological segment, the operator could map N skin surface regions immediately adjacent each anatomical location. These N surface regions could later be stitched together computationally to form the overall shape of the biological segment.

To improve upon the speed with which the operator of the untethered finger probe 150 can measure a biological segment's unloaded shape, multiple finger probes in the form of a data acquisition glove 170, can be used (See FIGS. 15A and 15B). For example, when all ten digits of the operator employ finger probes 150, the operator would place each of his fingers with a finger probe 150 at a marked starting point on the skin surface of a biological segment of interest, forming hand grasp postures on the biological segment. From that starting posture, the operator would then move his fingers gently across the surface of the skin, following the biological segment's contours. Using the same IMU 161 and force sensor 160 calculation, the X, Y, Z lab frame position trajectory of each finger probes' center of pressure would be computed, designating the contour of the biological segment beneath each finger probe's pathway across the skin. By repeatedly returning to the same left and right hand grasp postures, and repeating this finger movement pattern at a high resolution of skin points, the shape of the limb can ultimately be determined. To spatially couple each finger probe's skin trajectory to its neighboring finger probe trajectories within a single left or right hand glove, the position in 3D space of each finger probe 150 relative to adjacent finger probes needs to be measured. For this measurement, the IMU 161 on each finger probe 150 is required to measure the orientation (pitch, roll, yaw) of each finger probe 150. Further, additional sensors are required on the data acquisition glove 170. For example, additional IMU's placed on the middle or proximal phalanx of each digit are necessary to measure the hand grasp posture, and the linear distance between adjacent worn finger probes 150. Alternatively, by using dielectric material to form the data acquisition glove 170, wherein electrode traces are fabricated onto the dielectric material of the glove using a microfabrication methodology to form capacitive stretch sensors passing around the finger digits, measurements of digit flexion/extension and abduction/adduction could be made, and such measurements could be used to compute the linear distances between adjacent finger probes.

Step 3

Next, each untethered finger probe is used to estimate 1) the orthogonal impedance of body tissue at each anatomical point (viscoelastic map), and 2) the stress or strain tissue threshold where the subject first experiences discomfort at each anatomical point (sensitivity map). Each untethered finger probe is first pushed against the subject's body part (e.g. ankle-foot complex 172 in right image of FIG. 16) where the longitudinal axis of the finger probe is approximately perpendicular to the surface of the body at the point of contact. Using the untethered probe, or probes, tissue impedance can be estimated in one of two ways.

In a first method, the vibration actuator 151, is used to cause each finger probe 150 to vibrate. When the vibration actuator is activated, its motor spins an asymmetric mass that causes the finger probe 150 to vibrate. When finger probe 150 is in contact with a biological segment, these vibrations cause a force ripple against the tissue directly beneath the external cap's tissue force application (center of pressure point on external cap 152 due to tissue contact). The dielectric elastomer device 160 and processing unit 155 records such force ripples, and the IMU 161 and processing unit 155 records the accelerations caused by the vibrations. The acceleration data are then low pass filtered by processing unit 155 to estimate the maximum tissue compression and time rate of change of compression. Subsequent to tissue palpation, the measured force signal from force sensor 160 is combined with the tissue compression, and rate of compression, to estimate tissue mechanical impedance for that tissue region underlying the hemispherical external cap 152 of each respective finger probe or probes. This estimation computation is performed using finite element modeling to capture the continuous viscoelastic nature of biological tissue.

In a second method, the IMU 161 is used to estimate a change in tissue state (position and speed) by performing a zero velocity update when the finger probe is held stationary (zero acceleration except for gravity) against the tissue and then integrating. An LED on processing unit 155 is used to inform the probe user of the zero velocity update status. Once the zero velocity update is complete, the LED turns green from red, and the user of the finger probe then quickly pushes against the tissue, applying a greater force and tissue compression. By integrating forward the change in probe position in 3-D space can be estimated, and if the biological segment does not translate, the amount of tissue compression can be determined. Simultaneous to this estimate of tissue compression, and compression rate, the finger probe measures the applied force on the biological segment. Subsequent to tissue palpation, the measured force signal from force sensor 160 is combined with the tissue compression, and rate of compression, estimate from the IMU 161 calculation to estimate tissue mechanical impedance for that tissue region underlying the hemispherical external cap 152 of each respective finger probe or probes. This estimation computation is performed using finite element modeling to capture the continuous viscoelastic nature of biological tissue. It is important to estimate tissue impedance using tissue compression data from only the first moments after the zero velocity update. Preferably only the first 0.3 seconds of data after the zero velocity update should be used, as later times would result in tissue compression errors that are too great due to drift in the displacement estimate.

Since the pattern of skin speckles (Step 1) is unique at each anatomical location across the biological segment, a single camera image from mounted camera 154 taken of a small region of the skin surface can be used to determine the anatomical position at which the camera's lens is pointed or directed. Since the geometric position of camera 154 is fixed relative to the external finger cap 152 (and corresponding ultrasound probe 153), the anatomical location of the application of each finger probe on the body can be determined (assuming the probe user pushes on the body in a direction that is perpendicular to the body's surface). As noted previously, such an anatomical-positioning algorithm is achieved by comparing the single, anatomically-local image to the full speckle patterns across the entire biological segment determined in Step 2. With such a positioning algorithm, the biological limb can move during the times when impedance measurements are not being made without having to measure such limb movements. However, during an impedance measurement the biological limb has to remain stationary in a global sense if the biological segment's global position is not being tracked or measured.

A practitioner/clinician/subject using the instrument pushes each finger probe against a body surface of interest where each probe's orientation in contact with the body is approximately perpendicular to the body's surface at the point of probe force application. An example is shown in FIG. 16 where two 5-digit finger probe systems, or gloves 170 and 171 are shown. Here several finger probes are pressed against the subject's ankle-foot complex 172. As shown, the right hand 171 has a finger probe that exerts a force equal to but opposite the finger probes of the left hand 170. Through this apposing alignment between the two probe gloves, the forces applied on the body segment sum to zero since the user of the gloves, or probe operator, exerts equal and opposite forces where all finger probe forces sum to zero. With the net external force applied equal to zero, the biological limb's effective center of mass remains stationary, where the internal bones of the limb do not accelerate when the limb's external tissues are being compressed by the finger probes. If the user of the finger probes is careful to balance applied forces from the probes onto the biological limb, the limb will not translate and thus, measuring the position and orientation of the biological limb (e.g. 172 in FIGS. 16A and 16B) may not be necessary. If there is a risk that the biological limb will translate and/or rotate during tissue-compression experiments, technologies can be used to measure the limb's full orientation in 3-D space. For example, passive reflective markers can be positioned on the biological limb, and a camera or cameras can be mounted on the finger probe glove (170, 171 in FIGS. 16A and 16B) in order to measure the x, y, z locations of these passive markers relative to lab frame in 3-D space. If there is great translational/rotational limb bone movement during impedance/sensitivity measurements, such movements have to be measured, so as to determine accurately the amount of tissue compression caused by the finger probe force. In this case, the translation of the biological limb bone structure along the longitudinal axis of the finger probe 150 has to be subtracted from the measured finger probe 150 displacement upon tissue force application to determine an accurate measure of tissue impedance and sensitivity strain threshold. Other technologies can be used to determine the position of the biological limb during probe measurements including, but not limited to, electromagnetic signals, accelerometers, gyroscopes, magnetometers, active markers on the biological limb and receivers positioned off the limb in lab frame, or any other location technology or combination of location technologies.

In addition, the finger probe of Embodiment IV uses ultrasound to image the body to ascertain internal tissue properties and blood flow and nervous tissue transduction dynamics, and how such dynamics change as increasing force is applied on the tissue by finger probe 150. The ultrasound transducer 153 is used to gather very detailed tissue density data, soft tissue depth (orthogonal distance from the bodies surface to the bone), and blood flow dynamics. Since the finger probe measures force applied to the external finger cap 152 simultaneous with the ultrasound measurement, more accurate ultrasound data can be acquired. Since the ultrasound signal changes with applied force, or pressure, between the ultrasound head and the tissue being imaged, ultrasound data can be compared between distinct anatomical points at a fixed level of applied force, increasing the consistency and repeatability of the ultrasound data. This combination of force sensing and ultrasound sensing also enables the probe operator to measure blood flow just beneath each ultrasound probe, along the projection of longitudinal axis of finger probe 150 into the biological segment, as a function of applied finger probe force to determine how blood dynamics may be altered upon increasing applied external force.

Finally, the stress or strain tissue threshold where the subject first experiences discomfort at each anatomical point is measured to produce a sensitivity map. Here the subject verbally reports his/her level of discomfort with each applied probe force for each anatomical point at which probe force is applied. When the subject first reports discomfort at each anatomical location, that applied force and tissue strain is recorded and later used to create a sensitivity map.

As shown in FIGS. 16A and 16B, to increase the speed with which a biological segment can be mapped, many finger probes can be employed, for example, up to 10 finger probes, one for each finger on the right and left hands of the finger probe user. A plurality of finger probes can map a biological limb faster than the single probe of embodiment I, without the disadvantages of Embodiment II, namely poor orthogonality and specificity. Since each finger probe is controlled by a biologically-actuated finger, orthogonality can be achieved where each finger probe applies a force perpendicular the body's surface. In addition, since each biological finger is independent in its force application and position, at each anatomical location the stress/strain threshold when a subject first experiences discomfort can be determined.

Other advantages of the untethered finger probe include its spatial versatility, its proximity to the biological member being mapped, and its ease of transport. Since the finger probe has sensors located directly on each finger tip, and given the fact that the probe is untethered, affords it great spatial versatility; difficult areas of the body can be mapped where there is little space for a bulky, tethered instrument with a flexible arm. For example, if the upper thigh needs to be mapped in the case of a transfemoral prosthetic socket or leg exoskeleton, the untethered finger probe can readily take measurements in the medial crotch area without risk that the flexible arm will interfere, or block data collection in some way. The finger probe also has an improved proximity to the biological member compared to other types of instruments, e.g. Embodiment I and II. Since the force, ultrasound, IMU and photogrammetric sensors are located on the biological finger tip, the distance from the fingers to the biological segment being mapped is relatively small, allowing the user of the instrument to more readily palpate the biological member during data collection. Finally, the untethered finger probe is readily transportable; without the need for a flexible arm or tether, the finger probe, or probes, could be thrown into a backpack, for example, and employed to map the biological segment of a subject located in a remote area of the world.

Step 2: Mapping Biological-Limb Model Representation to Mechanical Interface Shape and Viscoelastic Properties Mapping Skin-Strain Model to the Tensile Viscoelastic Properties of the Mechanical Interface Understanding how the skin is stretched as a body segment is moved is paramount to mechanical interface design. As an example, in the case of a transtibial leg amputation, FIGS. 5A, 5B and 6A, 6B, 6C clearly show relatively large longitudinal skin strain at, and just proximal to, the patella, as well as large circumferential strains proximal to the knee joint when the knee assumes a flexed posture. Using conventional prosthetic socket technology, an amputee typically wears a liner that is rolled across the residual limb. By making the coefficient of static friction high between the skin and liner materials, designers have effectively lowered relative movement at that interface, reducing uncomfortable rubbing and chaffing. However, current liner technology does not comprise continuously varying tensile material properties that are informed by a skin-strain model as described in the previous section. Consequently, in areas of large skin strain, inflexibility in the liner causes skin discomfort due to high skin shear stresses imposed by the liner material. For example, in the case of a transtibial amputation, inflexibility in the liner in the high strain regions, or the patella and proximal knee areas, cause skin discomfort, especially when an amputee sits with knees flexed for an extended period of time.

In one embodiment of the present invention, we propose a liner that applies minimal shear stress on the skin when the biological segment changes posture, minimizing discomfort at the skin-interface junction. To achieve this goal, the mechanical strain energy stored within the liner is minimized when the biological limb is moved to a pose with large skin strains. We achieve this goal by continuously adjusting the tensile viscoelastic properties of the material spatially across the liner surface.

As an example, for the case of a transtibial amputation as shown in the skin-strain model of FIGS. 6A, 6B, 6C, large tensile skin strains are clearly visible longitudinally at, and proximal to, the knee patella. In this region of the residual limb, the skin-strain triangles are stretched longitudinally, or along the long axis of the thigh, indicative of the skin being under a large tensile stretch in that direction (detail B in FIG. 6C). In this region, the liner should be more stiff along the directions of minimum strain, indicated by the blue vectors, and less stiff along the red vectors representing maximum strain. This would serve to support the knee around the patella but permit knee flexion. In addition, due to muscle contractions upon knee flexion, large tensile skin strains are clearly visible circumferentially in the region of the leg proximal to the knee joint (detail A in FIG. 6B). Here, the proposed liner should permit circumferential expansion of the limb and be stiffer along the thigh's axial direction. The corresponding liner material adjacent to these large skin strain directions would be fabricated with a proportionally-small stiffness and damping, so as to minimize the amount of shear forces against the skin when the knee is flexed. In this invention, we teach of using a quantitative mapping from the skin-strain model to the corresponding tensile viscoelastic properties of the adjacent liner.

In the skin-strain model described in the previous section, a line connects each black-dot to an adjacent black-dot. In the modeling methodology, a strain is computed for each of these dot-to-dot lines, forming a whole grid of interconnected triangles (See FIG. 6A). In one embodiment of the present invention, the stiffness of the adjacent liner material to tensile stretch is numerically computed along the line between each set of two black-dot points, or each leg of a skin-strain triangle. The numerical relationship could be linear or nonlinear depending upon the type of mechanical interface, the region of the body for which an interface is to be constructed, and the specific needs of the user. In one embodiment, the mapping from the skin-strain model to the liner tensile viscoelastic properties is linear; liner stiffness along each leg of a skin-strain triangle is inversely proportional to the computed maximal skin strain, namely, where the skin strain is large, the corresponding tensile liner stiffness is small. Further, where the skin strain is small, the corresponding tensile liner stiffness is large. In one embodiment, in regions of large skin strain, a black-dot to black-dot stiffness equal to zero could be preferable, or alternatively a small stiffness that does not cause skin discomfort when the joint is held at a large-strain pose for an extended period of time. It will be understood by those of ordinary skill in the art that such proposed relationships between skin strain and adjacent synthetic materials of a mechanical interface can be applied to any wearable garment, shoe or device. For example, an athletic shoe of this invention would comprise an inner sock liner with continually varying modulus properties directly correlated to the underlying skin strain values associated with joint movements.

Mapping the Biological-Limb Shape-and-Impedance Model to Mechanical Interface Shape-and-Impedance Properties: A Linear Model The human anatomy is complex and consists of multiple materials of different properties. For example, a transtibial residual limb consists of bones, (femur, tibia, fibula, and the patella), muscles (tibialis, gastrocnemius, peroneus longus, etc.) and other anatomical landmarks including, but not limited to, the tibial tuberosity, medial femoral condyle, lateral femoral condyle and the medial tibial flare.

In one embodiment of the present invention we employ a quantitative mapping between the viscoelastic properties of the body when the body is compressed orthogonal to the skin surface, and the corresponding properties of the mechanical interface.

For areas on the body for which an interface is to be designed, the underlying anatomical components and their viscoelastic properties are quantitatively related to the stiffness and damping of the adjacent mechanical interface. For one embodiment of the present invention, we will have an interfacing material adjacent to each anatomical location with inverse stiffness and damping characteristics to that of the body. Although an inverse linear mapping algorithm is used here, there could exist a nonlinear mapping including but not limited to parabolic, hyperbolic, trigonometric, exponential functions, and differential equations will create unique spatial material compositions within the mechanical interface for each anatomical location. The available tools are limited to automatically measure the body's stiffness and damping properties when a residual limb is compressed perpendicular to its skin surface. As such, in one embodiment of the present invention, we assume that the gross stiffness and damping properties of the body scale to the soft tissue depth at that anatomical point. Here soft tissue depth is defined as the orthogonal distance between the surface of the skin and the intersection of bone tissue when the body is not being compressed and is in a state of equilibrium. For boney protuberances such as the fibula head in the transtibial residual limb, the soft tissue depth is small and the body is stiff to orthogonal compression. In distinction, in the calf region the soft tissue depth is relatively larger and the body is relatively softer to orthogonal compression.

Figure 17:
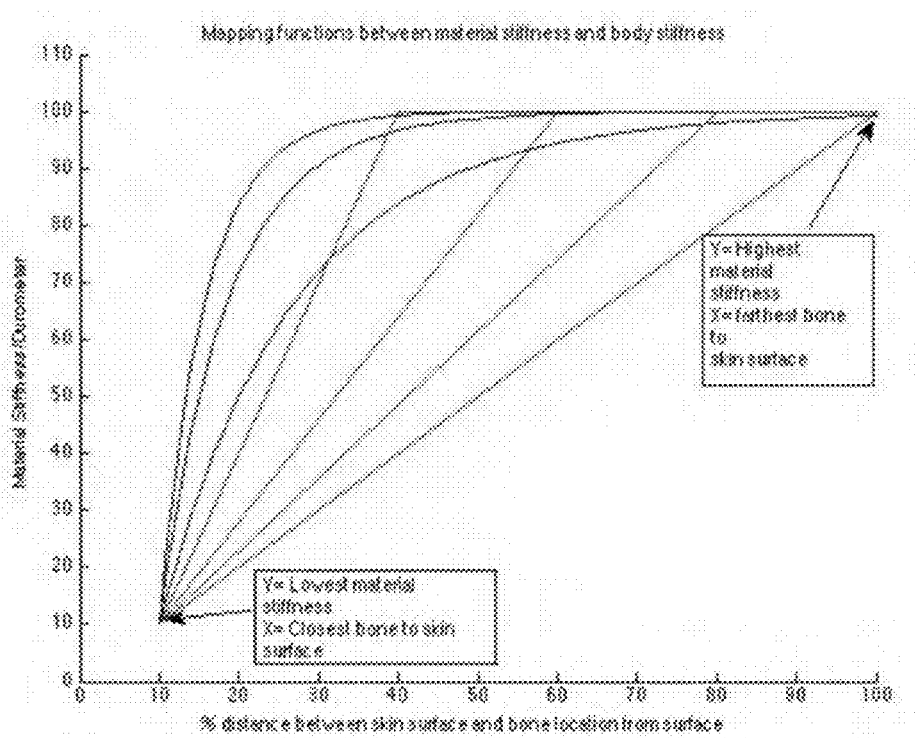
FIG. 17 is a graph showing linear and non-linear relationships between the body's viscoelastic properties as estimated from soft tissue depth plotted horizontally, and the corresponding durometer of the mechanical interface plotted vertically.

In one embodiment, the perpendicular distance from the skin surface to the bone obtained from MRI or other imaging data is used as a gross estimate of the body's viscoelastic properties. FIG. 17 shows the quantitative relationship between mechanical interface stiffness, or durometer, and body stiffness represented as the percentage of soft tissue depth. Here the horizontal axis is the soft tissue depth, D, normalized by the maximal soft tissue depth, $D_{max}$, multiplied by 100. Both linear and non-linear curves are presented showing the possible variation in the relationship between interface durometer and corresponding soft tissue depth. Generally, as soft tissue depth decreases, and body stiffness increases, the adjacent interface becomes increasingly soft. Where there are boney protuberances, the adjacent interface will be soft and compliant, but where the body is soft with a large soft tissue depth, the adjacent interface is designed to be more rigid.

Figure 18:
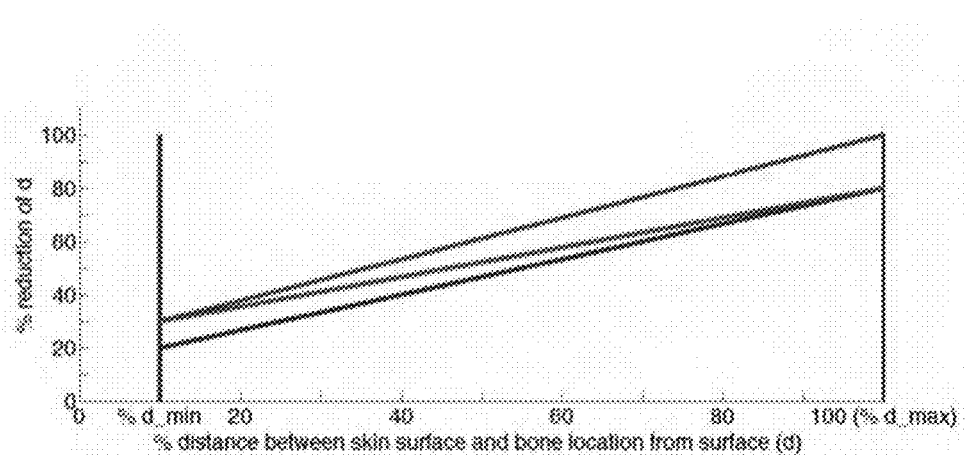
FIG. 18 is a graph showing relationships between the unloaded interface shape and tissue stiffness approximated here as soft tissue depth.

Another critical parameter that describes the mechanical interface design is the percent of soft tissue compression, namely the percent change in the soft tissue depth caused by the interface during a non-loaded state. In FIG. 18, the percent of soft tissue compression is plotted vertically, and the percent of tissue depth is plotted horizontally. Here the horizontal axis is the soft tissue depth, D, normalized by the maximal soft tissue depth, $D_{max}$, multiplied by 100. Further, the vertical axis is the soft tissue compression caused by the interface, normalized by the maximum soft tissue compression, multiplied by 100. Several linear curves are shown, depicting that as soft tissue depth increases, the amount that the interface compresses the tissue increases. Although only linear curves are shown in FIG. 18, additional embodiments could include nonlinear relationships such as parabolic, hyperbolic, trigonometric, exponential functions, and differential equations. Generally, where the body is soft, or where soft tissue depth is high, the interface will compress the tissues more. Where there is a boney protuberance, and the body is stiff with a small soft tissue depth, the interface will compress the tissues by a small amount or not at all. Such an inverse relationship between body stiffness and tissue compression results in a more uniform pressure field across the residual limb surface.

It will be understood by those of ordinary skill in the art that the level of tissue compression by the mechanical interface may depend upon anatomical location. For example, when there are underlying nerves and vessels that may be more sensitive to external pressure, the level of tissue compression by the interface will have to be reduced accordingly. A single curve mapping the level of tissue compression to body viscoelastic properties may not be universally applied across the entire biological segment, but may vary as a function of anatomical location. Clearly, a plurality of curves may be required to fully capture the quantitative mapping between tissue compression levels, body viscoelastic properties and anatomical location.

Mapping the Biological-Limb Shape-and-Impedance Model to Mechanical Interface Shape-and-Impedance Properties: An Optimization Procedure In the previous embodiment, linear mappings (FIGS. 17 and 18) were often assumed, relating the output of the shape-and-impedance biomechanical model to a numerical description of the interface's shape and impedance properties. In this section, a mathematical optimization framework is presented for defining the mapping that does not assume linearity a priori. The procedure employs the digital anatomical data of that part of the body for which an interface design is sought, to attain that interface shape and impedance that produces a uniform interface pressure applied to the biological limb, and a minimized spatial pressure differential in the presence of atrophy by the biological limb.

Before presenting the optimization procedure, we define key variables:

A. From a set of digital points $\vec{S}_i^{\,v}(X,Y,Z)$ located on the surface of the biological limb to be interfaced with a mechanical device, create a 3D volume. Here Z is in the direction of the gravitational vector, whereas X and Y are perpendicular to the Z-axis and to each other.

B. From three neighboring points or vertices $\vec{S}_1^{\,v}(X,Y,Z)$, $\vec{S}_2^{\,v}(X,Y,Z)$, and $\vec{S}_3^{\,v}(X,Y,Z)$, define the area vector ($\vec{A}_i$) of each triangle, within the grid, directed outwardly and orthogonally from the surface of the biological limb. Note the origin of area vector $\vec{A}_i(X,Y,Z)$ is located at the center of area at point $\vec{S}_i(X,Y,Z)$.

C. Define the unit area vector as $\vec{e}_i = \vec{A}_i/A_i$, or the area vector divided by the magnitude of the area vector. This unit vector is directed outwardly and orthogonally from the center of area of the section defined by the three neighboring vertices $\vec{S}_1^{\,v}(X,Y,Z)$, $\vec{S}_2^{\,v}(X,Y,Z)$, and $\vec{S}_3^{\,v}(X,Y,Z)$.

D. Define the angle $\theta_i$ between the line of the unit area vector and the vertical Z-axis.

E. Define the total area at the top of the socket in the Z direction, or $A_{Z\_top}$. A simplified approach to estimate $A_{Z\_top}$ is to assume a circle defining a plane that is orthogonal to direction Z, with a diameter equal to the average diameter of the residual limb adjacent the socket's upper, or most proximal, brim or cutline. More rigorously, $A_{Z\_top}$ is the total area in the Z direction of the adjoining surface connecting the line around the residual limb surface at the upper, or most proximal, brim or socket cutline.

F. Calculate the uniform Pressure ($P_{uni}$) within the prosthetic socket. It is approximated as $P_{uni}=W/A_{Z\_top}$ for a transtibial or transfemoral socket for a person in quiet, single-leg standing with body weight W. Alternatively, as a worst case, one could assume a uniform pressure equal to $3W/A_{Z\_top}$. Here the factor of 3 is an estimate of the dynamic loading experienced during running.

G. Calculate the vector force ($F_i$) parallel but oppositely directed from area vector ($\vec{A}_i$) from the uniform socket pressure ($P_{uni}$)

$$\vec{F}_i = -P_{uni} * \vec{A}_i$$

H. Determine the residual limb impedance $I_i$ with stiffness $K_i$ and damping $B_i$ components of each node point $\vec{S}_i(X,Y,Z)$ at the center of area $\vec{A}_i$ (impedance is based on the mechanical properties of skin, muscle, fat and bone measured in the direction of the applied Force vector, $\vec{F}_i = -P_{uni} * \vec{A}_i$)

I. Calculate $\vec{r}_i(\Delta X, \Delta Y, \Delta Z)$ to get the new point $\vec{S}_i(X,Y,Z)^*$. The 3D volume from the set of points $\vec{S}_i(X,Y,Z)^*$ determines an optimal shape of the socket at load $\vec{F}_i = -P_{uni} * \vec{A}_i$ that achieves a uniform-socket, residual-limb interface pressure.

1. $\vec{r}_i = \vec{S}_i(X,Y,Z)^* - \vec{S}_i(X,Y,Z)$

2. For one embodiment, we estimate $\vec{r}_i(\Delta X, \Delta Y, \Delta Z)$ by assuming a linear approximation for body stiffness, or $K_i = C_i * d_i$ where $d_i$ is the scalar soft tissue depth defined as the distance from the center of area at $\vec{A}_i$ on the surface of the residual limb at point $\vec{S}_i(X,Y,Z)$ to the surface of the bone measurable using MRI, and $C_i$ is a proportionality constant between body stiffness $K_i$ and the distance $d_i$. Thus, $\vec{r}_i = \vec{F}_i/(C_i * d_i)$.

Optimization

The procedure thus far estimates the shape of the residual limb $\vec{S}_i(X,Y,Z)^*$ under a uniform pressure, $P_{uni}$, with a load at each node equal to $\vec{F}_i = -P_{uni} * \vec{A}_i$ and the amount of tissue compression at that load, or $Y_i = -P_{uni} * \vec{A}_i/(K_1)$. Using a simplified model for estimating body stiffness $K_i = C_i * d_i$, we have $\vec{r}_i = -P_{uni} * \vec{A}_i / (C_i * d_i)$. Since $P_{uni}$ $W/A_{Z\_top}$, $\vec{r}_i = -(W/(A_{Z\_top} C_i d_i)) * (\vec{A}_i)$. However, what is still unknown is the optimal interface impedance, or for a static load assuming quiet standing, the optimal interface stiffness $k_i$. In this example, the damping force term $b_i * \vec{V}_i$ is not a consideration since it is a statics problem with tissue compression velocity $\vec{V}_i$ equal to zero. To optimize the stiffness of the socket interface $k_i$ at each interfacing node $\vec{S}_i(X,Y,Z)^*$ at pressure $P_{uni}$ that yields a constant socket pressure in a variable-impedance socket, we minimize the pressure differential ($\delta P/\delta Z$), or the change in interface pressure along the surface of the residual limb in the Z direction in the presence of an atrophy or hypertrophy disturbance.

A. The socket interface stiffness $k_i$ describes the stiffness of the interface adjacent to node i.

B. The amount of interface elastic compression at node i is equal to:

$$\vec{s}_i = \vec{F}_i / k_i = (-P_{uni} * \vec{A}_i) / k_i = (-W/A_{Z\_top} * \vec{A}_i) / k_i$$

C. Consider that the residual limb has changed shape at the zero load condition from $\vec{S}_i(X,Y,Z)$ to $S_i^d(X,Y,Z)$ due to residual limb atrophy or hypertrophy. We can define an atrophy or hypertrophy disturbance vector $\vec{a}_i$ as $$\vec{a}_i = \vec{S}_i^d(X,Y,Z) - \vec{S}_i(X,Y,Z).$$

D. In one embodiment, the disturbance vector is equal to:

$$\vec{a}_i = -D_i * d_i * \vec{e}_i$$

where $\vec{e}_i = \vec{A}_i / A_i$ defined earlier, $d_i$ is the soft tissue depth defined earlier, and $D_i$ is a proportionality constant. We assume here that the atrophy or hypertrophy disturbance is orthogonal to the residual limb surface at node i, and is proportional to the soft tissue depth at that point.

E. After the disturbance, the interface spring compression would be:
1. $\vec{T}_i = \vec{s}_i - \vec{a}_i - \Delta Z_i(\vec{g}/g)$ and the force at node i would be $\vec{F}_i = k_i [\vec{s}_i - \vec{a}_i - \Delta Z_i(\vec{g}/g)]$
2. Here $\Delta Z_i = [W - \Sigma_i [k_i(\vec{s}_i - \vec{a}_i) \cdot \vec{g}/g]] / [\Sigma_i [k_i \cos \theta_i]]$
3. After the disturbance, the pressure field is no longer uniform, and is equal to:

$$P_i = \vec{F}_i / \vec{A}_i$$

4. Minimize the pressure differential $$\frac{\partial P_i}{\partial Z}$$

in the Z direction along the surface of the body from node to adjacent node by varying node stiffnesses $k_i$ 5. For the array of interface stiffnesses $k_i^{min}$ that minimize $$\frac{\partial P_i}{\partial Z^{min}},$$

identify $S_i(X,Y,Z)^{}$ that gives the new interface equilibrium (unloaded) shape, or a. $S_i(X,Y,Z)^{} = \vec{s}_i + \vec{S}_i(X,Y,Z)$ where
b. $\vec{s}_i = \vec{F}_i / k_i = (-P_{uni} * \vec{A}_i) / k_i^{min} = (-W/A_{Z\_top} * \vec{A}_i) / k_i^{min}$ Step 3: Mechanical Interface Fabrication The most advanced prototyping and CAM technology on the market will be used to seamlessly integrate spatially-varying viscoelastic properties into the mechanical interface design. It is understood by those of ordinary skill in the art that the final mechanical interface can be manufactured using both traditional and state-of-the-art methods including, but not limited to, casting, 3D printing, mechanical linkages of disparate materials and shape deposition manufacturing.

Fabrication of Tensile Viscoelastic Properties

It will be understood by those of ordinary skill in the art that liner viscoelastic properties can be varied spatially in a number of ways, including but not limited to, varying liner thickness, density, material composition and type, and/or material structure (e.g. through the use of small material hinges across the liner surface).

In one embodiment, liner thickness is varied to accomplish spatial viscoelastic variation. Here each strain triangle leg (as an example see FIGS. 6A-C) has a corresponding thickness of the liner inversely proportional to the maximum skin-strain computed. In another embodiment, the numerical mapping computes the average of the three skin strains corresponding to each leg of a skin-strain triangle (an example is shown in FIGS. 5A, 5B), and then an inversely-proportional relationship defines the corresponding liner thickness at that triangular region.

In another embodiment, a plurality of different material types are employed within the liner. Along each leg of a skin-strain triangle for which large strains occur, a thin compliant material is employed within the liner, while adjacent the small-strain leg of a skin-strain triangle a separate material is attached to further increase the liner thickness and stiffness in such regions. For example, in the transtibial residual limb case, shown in FIGS. 6A-C, for the area proximal to the knee joint the skin is stretched circumferentially but not longitudinally along the long axis of the thigh upon knee flexion. The adjacent liner could comprise of a thin compliant material spanning the entire region, and attached to it strips of added material running longitudinal to the long axis of the thigh. When the thigh muscles contract and expand upon knee flexion, and the skin stretches circumferentially, the thin, compliant liner material would accommodate this stretch with minimal shear force applied to the skin, while the longitudinal strips would add structural integrity to the liner interface. In distinction, for the patella, and the region just proximal to the patella, shown in FIG. 6, the skin stretches longitudinally but not circumferentially as the knee assumes a flexed posture. In such regions, the thin strips of added material would run circumferentially, while the underlying thin, compliant material would connect adjacent strips, allowing the skin to stretch longitudinally upon knee flexion with minimal shear stress applied to the skin.

Fabrication of Compression Viscoelastic Properties

Various methods have been suggested to relieve pressure over bony protuberances and other anatomical landmarks in passive prosthetic sockets. In conventional approaches, different materials have been bonded or mechanically attached together to relieve pressure on anatomical protrusions. Other CAD/CAM methodologies include the use of double walls, and most recently, the creation of mechanical compliant features in a 3-D printing process.

In one embodiment of the present invention we employ variable impedances seamlessly integrated into socket production using advanced 3D printing technology. 3D printing has been used in design of medical technologies for decades. However, the methodologies and capabilities of the machines have continued to evolve. Objet Geometries Inc. (North America, 5 Fortune Drive, Billerica, Mass. 01821, USA, T: +1-877-489-944) produces the most advanced 3D printer that uses their PolyJet Matrix™ Technology. In FIG. 19, the Objet Connex500 is shown. This technology enables different material durometers to be simultaneously jetted in the production of the same mechanical interface, allowing for spatially varying viscoelastic properties across the interface surface. With a16-micron, high-resolution print layer, high dots-per-inch in both X and Y resolution, and an easy-to-remove support material property, this technology is ideal for the development of prosthetic and orthotic prototypes.

There is a relatively large library of standard materials used by the Connex family of 3D printers. In addition, composite materials can be created to produce Digital Materials™ to give a wide range of material properties; a desirable feature in prosthetic and orthotic designs mapped from calculated biological limb stiffness and damping properties.

Shown in FIGS. 20A-20P is an example of how an Objet 3-D printing process can be employed in the fabrication of a prosthetic socket prototype for a transtibial amputee. In the first (FIGS. 20A-20D) and second row (FIGS. 20E-20H), MRI images and corresponding soft tissue depth models are shown for the right leg of a transtibial amputee. Orientation from left to right for all images are anterior, lateral, medial and posterior, respectively. Acquired MRI data are used to design the varying viscoelastic features within the socket wall.

As with FIGS. 7A-C, the second row FIGS. 20E-20H shows different views of the soft tissue depth model of the residual limb. As defined earlier, the soft tissue depth is the orthogonal distance D between the skin surface and a bone intersection. Here, red regions show large tissue depths, yellow regions moderate depths, and green regions relatively small depths. For these depth models, the patella tendon was removed, exposing the soft tissue depth in the region of the patella tendon just distal to the patella (shown as the red region in the left-most image).

In the third row in FIGS. 20I-20L, different views of a 3-D printed prosthetic socket is shown where every material color corresponds to a material having a distinct durometer and tensile strength. Here, the red material has the highest durometer and tensile strength, while the green material has the smallest durometer and tensile strength. More specifically, Table 1 in FIG. 31 shows the mapping from soft tissue depth to interface material tensile strength. All these distinct compression viscoelastic features are integrated together seamlessly so that the sockets are manufactured in one piece with limited post processing requirements. The color mapping is used above with soft tissue depth being shown in millimeters (mm), and socket tensile strength in megapascals (MPa).

In the fourth row of FIG. 20.4, the socket's most rigid, high tensile strength material (shown in red in the third row) is modeled using an FEA analysis to evaluate structural integrity for vertical loads comparable to that which would be experienced during standing and walking. FIG. 21 shows the Von Mises Stress distribution and corresponding color code used in FIG. 20.4. Assuming a 3X body weight vertical loading, the wall thickness of the red material shown in the third row was varied to achieve an acceptable level of material stress. Additionally, the two struts, or bars, that connect the patella tendon region of the socket to the distal socket base are included to achieve structural integrity; without these struts, the socket would be under risk of collapsing upon vertical loading when the amputee stood or walked with the socket interface.

Referring now to FIG. 22, the linear relationship used in the socket design and fabrication of FIGS. 20A-20P is shown. Here the quantitative mapping of interface modulus (plotted vertically) to soft tissue depth (plotted horizontally) is plotted, showing numerically how the interface becomes softer and softer as the body becomes stiffer and stiffer (with smaller and smaller soft tissue depths). More specifically, FIG. 22 shows the mapping between the Young's Modulus of socket interface materials shown in the third row of FIGS. 20I-20L to the soft tissue depth at each location shown in the second row of FIGS. 20E-H, where it is color coded by categories of soft tissue depth.

Manufacturing for Durability

The fabrication example shown in FIGS. 20A-20P is problematic because the Objet 3-D printed material is unstable, degrading in time with unfavorable mechanical properties. In this section, we propose a fabrication method that result in a more stable interface product.

Figure 23:
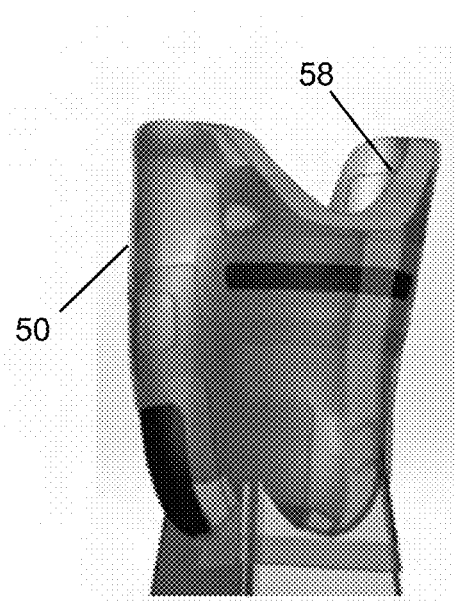
FIG. 23 is a transtibial socket design.

From the optimized set of material impedances ($k_i$), a transformational mapping is established for manufacturing using conventional processes including, but not limited to, molding, casting, shape deposition, and carbon composite lamination. In FIG. 23, a transtibial socket 50 is shown where each color represents a distinct material durometer or impedance. Such a variable-impedance socket layer can be fabricated using shape deposition processes or by modulating silicone durometer spatially using standard silicone fabrication procedures. The outer transparent element 52 is designed to transfer load from the variable-impedance socket distally, while still allowing deformation of the compliant regions of the socket 50. This outer element 52 can be made of carbon fiber and is used to ensure structural integrity while allowing flexibility in the regions where compliance is needed.

The ideal stiffness set $k_i$ for the mechanical interface can be produced with a spatially-varying impedance socket and integrated liner, encased in an outer carbon composite exoskeletal frame. In one embodiment of the present invention, a liner 54, or a thin polyurethane or silicone skin-tight sock, is bonded directly to the multi-material socket (See FIGS. 23 through 26), or can be attached and removed easily in a donning and doffing process using standard attachment means such as a mechanical pin lock. In another embodiment of the invention, the liner and socket shown in FIGS. 24 through 26 could be fabricated as a single piece using polyurethane in a shape deposition process, or urethane using standard urethane fabrication strategies, or silicone. Alternatively, the liner 54 and socket 50 could be fabricated separately, and then attached subsequent to fabrication. Still further, in another embodiment the inner surface of the variable-impedance liner adheres to the body's skin using a synthetic "gecko" material that increases the shear strength between the skin and the interface, while still allowing easy donning and doffing of the artificial interface.

Figure 24:
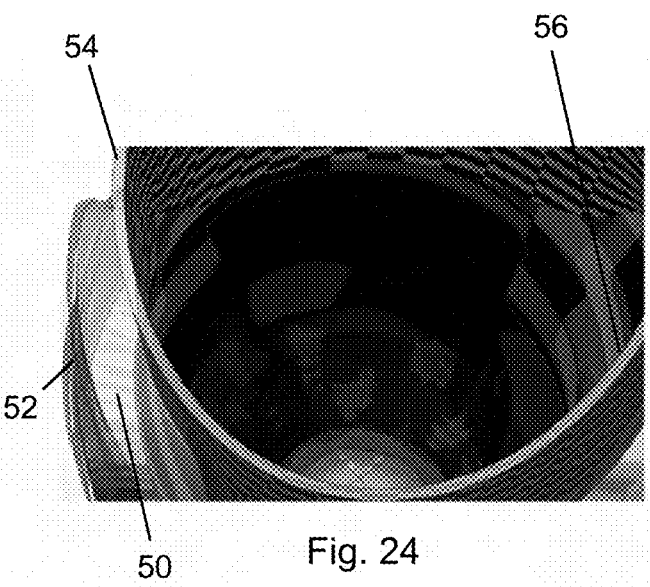
FIG. 24 shows a thin compliant material, or liner, bonded at its distal aspect to the multi-material prosthetic socket shown in FIG. 23 to form a fully-integrated mechanical interface with the body.

More specifically, in FIG. 24, a thin compliant material, or liner 54, is bonded at its distal aspect to the multi-material prosthetic socket 50 shown in FIG. 23 to form a fully-integrated mechanical interface with the body. On its inner surface 56, the liner 54 adheres intimately to the human body using a synthetic gecko material. The liner system, because of its intimacy with the body, and its continuity with the socket, fundamentally solves the issue of suspension within sockets, eliminating the need for a pin suspension or the like.

Figure 25:
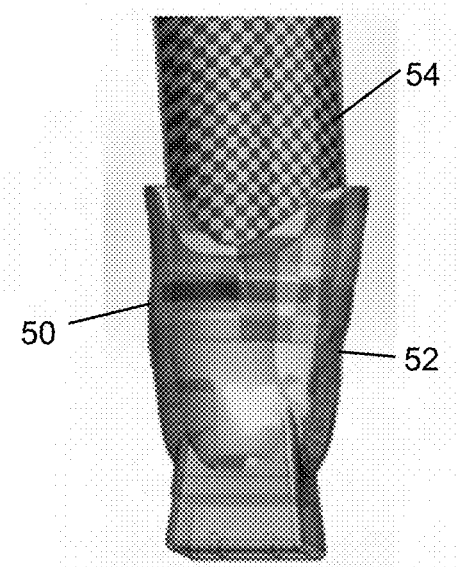
FIG. 25 is a full view of the multi-material prosthetic socket with the internal liner and socket bonded within and a carbon fiber outer material.

In FIG. 25, a full view of the multi-material prosthetic socket with the internal liner 54 and socket 50 bonded within and a carbon fiber outer material 52.

Figure 26:
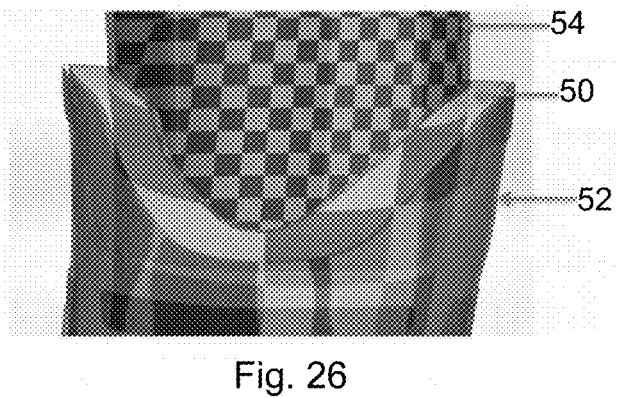
FIG. 26 shows the internal liner bonded to the inner surface of the variable-impedance socket within a carbon fiber element.

In FIG. 26, the internal liner 54 bonded to the inner surface 58 of the variable-impedance socket 50 within a carbon fiber element 52. Adjacent the compliant regions within the socket 50, the carbon fiber element 52 is spaced from the outer surface of the socket 50, so as to allow expansion of the socket 50 in those regions.

Figure 27:
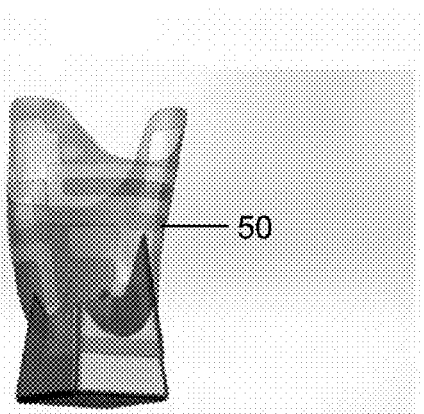
FIG. 27 is shows the outer carbon fiber element designed for structural integrity.

In FIG. 27, the outer carbon fiber element 52 is designed for structural integrity. The external element could be made from carbon fiber or any structural material capable of transferring loads to the external prosthetic limb. The gap size between the variable-impedance socket and the carbon fiber outer element is inversely proportional to the socket's stiffness, namely, where the socket 50 is relatively soft, the gap is large, allowing the compliant region of the socket 50 to expand outward upon load bearing. In distinction, where the socket 50 is relatively stiff, the gap is made relatively small, so as to allow the transfer of load from the variable-impedance socket to the carbon fiber external frame element.

It will be understood by those of ordinary skill in the art that the variable-impedance liner 54 and socket 50 in FIG. 26 could be fabricated by using a single material having a spatially-variable geometry, or by using multiple-material types. For example, the liner 54 of FIG. 26 could be fabricated with a uniform thickness but with multiple durometer silicones. Further, the socket 50 of FIG. 26 could be fabricated with a continuously-varying silicone thickness; where compliance is sought the silicone would be relatively thick, whereas where stiffness is sought, the silicone would be relatively thin. Such a silicone socket 50 wall that achieves a continuously-variable perpendicular modulus (correlated to the perpendicular tissue modulus at each anatomical point) by continuously varying it silicone wall thickness has many advantages, including a simple manufacturing process with stable and durable materials.

Fabrication of a Liner with Embedded Sensors

Continuous monitoring of physiological information within the socket liner can quantitatively inform socket fabrication and modification for the improvement of socket fit and comfort. In addition, such technology will provide previously unprecedented levels of information about the wearer's intent to aid in external bionic limb control. To achieve this level of monitoring, sensing electronics should be integrated into the liner itself. Wirelessly relaying sensed information from the liner material adjacent the residual skin to the external prosthetic socket element is ideal in order to avoid needing wires and electrical connectors passing from liner to external socket. There are two key related problems for integrating sensing capability into the compliant liner. First, there is the packaging problem of actually placing the front-end sensor (e.g. electromyographic (EMG) electrodes, force, pressure, shape, ultrasound, temperature, etc.) into the correct location relative to the body without causing discomfort or inconvenience to the wearer. Because such sensing modalities ideally should be located at the socket-skin interface, an ideal solution for packaging would be the integration of compliant, miniature, and wireless electronics near the location of the sensor-to-body interface, forming an inner liner membrane that is smooth, continuous, and with skin-like mechanical properties.

The second problem is power consumption in the electronics. Clearly, the elements of the sensors that are in the liner or liner equivalent must be very small. If the electronics are integrated alongside the sensing elements, then the small size limits the amount of available energy storage or available harvested power. A target size for integrated devices of a few $cm^2$ on a flexible substrate with minimal thickness would limit the energy budget to the range of 10's to 100's of Joules, 2-3 orders of magnitude less than a cell phone battery. The main problem is that off the shelf electronics for physiological monitoring, processing, and wireless communication tend to consume many milliWatts of power (10s of mWs for most commercial radios). This power problem is prohibitive to integrating wireless electronics in the socket liner without a dramatic reduction in circuit power consumption.

In this section, the design and fabrication strategy of a liner (liner layer 54 shown in FIG. 26) is described that employs a dielectric elastomer. While dielectric elastomers have often been used for actuation and power generation, they can also be used as an integrated sensor. When a dielectric elastomer device (dielectric elastomer material with imbedded compliant electrodes) is mechanically deformed, both the capacitance and dielectric resistance of the material is changed. Thus, compliant electrodes are microfabricated within the dielectric elastomer liner material to measure mechanical forces (normal and shear) applied to the residual limb, and residual-limb, volume and shape changes. In addition, compliant electromyographic (EMG) sensors are embedded within the liner for sensing muscle activity for the control of active bionic joints.

Figure 28:
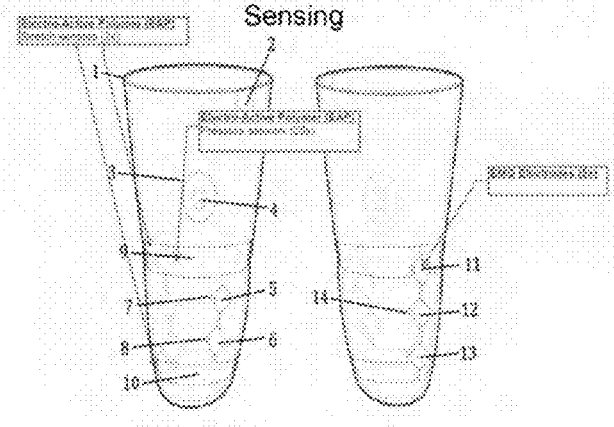
FIG. 28 shows a front view of the liner embedded with sensing modalities.

In FIG. 28, a line drawing of the liner 1 is shown depicting the location of sensors and the electronic board 2 where sensing modalities are embedded within liner 54. The board 2 houses the liner electronics and includes EMG amplification, A/D conversion, signal conditioning, and an antenna for wireless communications. Embedded within the wall of the silicone liner are all sensors, electronics, and wiring such that the inner surface of the liner is smooth and continuous so as not to cause discomfort to the wearer. EMG sensors are soft, flexible electrodes shown at 5, 6, 11, 12, and 13. A commercial electrode can be used, e.g. from SmartTrace (1015663—SmartTrace Electrodes, Hospital Version). Electrodes are positioned over the muscles of the residual limb. Muscle locations can be determined from residual limb MRI or other imaging data. EMG electrode 4 is positioned on the patella 3 for grounding. Before donning the liner, the residual limb is sprayed with a bio-compatible adhesive for improved adhesion between the electrodes and skin.

Stretch sensing dielectric elastomers are used within the liner for the measurement of forces applied on the residual limb from the liner and socket. In addition, sensors are positioned within the liner to measure circumferential shape changes. When such a device, (elastic polymer with compliant electrodes), is mechanically deformed, both the capacitance of the device, as well as the electrode and dielectric resistance, are changed. Such a sensor offers several potential advantages over traditional sensors including operation over large strain ranges, ease of patterning for distinctive sensing capabilities, flexibility to allow unique integration into components, stable performance over a wide temperature range and low power consumption.

Components 7, 8, and 14 are representative patterned electrodes for the measurement of liner forces in both normal and shear directions. Here the silicone for force sensing is positioned between two electrodes, one beneath the material layer, and a second on top of the material lay, forming a sandwich where the electrodes are the "bread pieces" and the silicone is the "meat". Such a dielectric sensor measures changes in capacitance when the silicone material is compressed under an externally applied pressure, and/or stretched causing the distance between the electrodes to become smaller. Additionally, a dielectric sensor is used to measure circumferential changes of the residual limb. Bands 9 and 10 are stretch dielectric sensors using the dielectric sensor approach described earlier. Within the walls of the silicone liner, wires or microfabricated conductive traces pass from each electrode to processing board 2 (wiring not shown in FIG. 28). Sensory data are then transmitted to a receiver located on the external prosthesis.

EMG sensing is employed as the basis for controlling and modulating the response of a powered prosthesis. The liner is designed based upon such EMG control requirements. The EMG electrodes are placed on the liner in a way to detect dorsiflexor (eg. Tibialis Anterior) and plantar flexor (eg. Soleus and Gastrocnemius) muscle activity in the residual transtibial limb with these being used to signal the movement intent of the wearer. For instance, the EMG activity may signal intent to position the ankle into a dorsiflexed or plantar flexed position (joint equilibrium), to point the prosthetic foot upwardly while ascending stairs or a hill, or to point the prosthetic foot downwardly so as to lift the wearer within reach of an object, or to point the toe while walking down stairs, for instance.

The EMG activity detected in the dorsiflexors may also signal the need for increased stiffness and damping, together the impedance, in late swing or early stance as might be needed to absorb energy (brake) while walking down a steep hill, for instance. The EMG activity detected in the plantar flexors during mid-to-late stance may signal intent to walk fast, to run or to walk cautiously down a steep hill or stairs. Here, rather than controlling the ankle angle directly, the EMG activity can be used to modulate the gain of the positive-torque feedback reflex response in the ankle prosthesis in accordance with wearer intent. To accomplish the modulation functions noted above, we transmit to the external active prosthesis the EMG signal from all five locations at the rate of 125 Hz.

As noted earlier, the liner employs dielectric capacitance-based sensors as the basis for quantitative measurement of socket force and limb shape/volume over time. Without loss of generality, such sensors can also be used to monitor heart rate that will inform the level of exertion during the day and over time. This information is logged in the non-volatile memory of the prosthesis so that the clinician can observe the historical record of force (stress) and residual limb expansion/contraction (residual limb shape/circumference) to inform the need for an intervention—a socket modification or a new socket, for instance.

Figure 29:
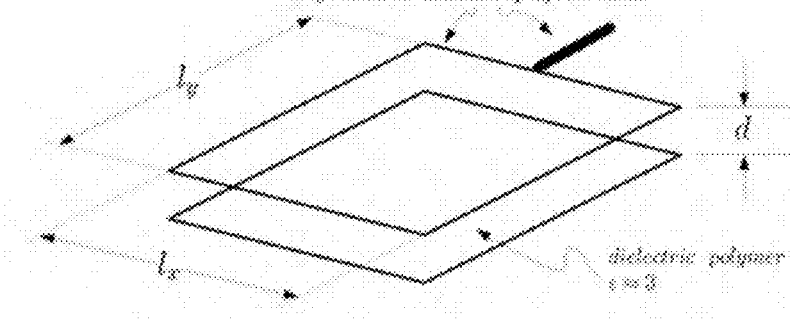
FIG. 29 shows an electro-active polymer electrode.

As described in the previous subsection, the liner described herein comprises dielectric capacitance-based sensors to measure limb circumference and force. These transducers comprise force sensors and stretch sensors each using a capacitance measurement method to infer axial or longitudinal deflection. The EAP capacitance, $C_{EAP}$, is defined as follows:

$$C_{EAP} = \frac{\epsilon \epsilon_0 A}{d}$$

where $\epsilon_o$ is the dielectric in a vacuum and c is the dielectric constant of the polymer liner. A is the sensor electrode cross-sectional area defined as the product of the longitudinal dimensions, $l_x$ and $l_y$, and d is the thickness of the dielectric between the electrodes as shown in FIG. 29, which is an illustration of and electro-active polymer electrode.

For the force sensing application, the capacitance change arises from the compression of the dielectric, decreasing the thickness, d. For the liner application, carbon black electrodes are printed roughly 10 mm×10 mm with a sensor thickness of approximately 100 µm thick. Assuming a dielectric constant of about 3, the nominal (zero deflection) capacitance will be roughly 30 pF. For the stretch application (upper) an electrode will be printed approximately 150 mm long and 10 mm wide—yielding a capacitance of approximately 130 pF. The corresponding lower stretch band is approximately half the length of the upper band, the capacitance will be roughly 65 pF. Assuming a typical deflection of 10% in both the force and stretch applications, sensing circuitry is required that can detect capacitance changes with a precision of better than 1%, or about 0.25 pF.

To accomplish this, circuitry is employed to measure changes in the time constant, $\tau_{EAP}$, using an AC drive (~20 kHz square wave for the pressure sense and ~4 kHz for the stretch sense) with large source impedance (~1 MΩ). The 0.25 pF precision is achieved through detection of the time constant change, $\delta\tau_{EAP}$, of approximately 250 nsec, or about 1/200 of the excitation period. Two methods are proposed for making the capacitance measurement. One employs an RMS measurement of the differential signal, using the fact that the RMS value of the signal should be proportional to $$\frac{1}{\tau_{EAP}}.$$

In the other method, a comparator and low-pass filter is applied to measure implicitly the pulse-width of the comparator output that is proportional to $\tau_{EAP}$. In either case, the duty cycle of the measurement is quite low since the measurement would be made 5-10 times per day when the wearer is standing but not moving. Here an RMS measurement of socket pressure at all twenty locations and both upper and lower stretch could be made over a period of a second and then reported to the external prosthesis where it could be stored in non-volatile memory. Such would give the clinician a daily historical record from which trends relating to goodness-of-fit could be discerned. Further, force and circumference sensory information, in addition to EMG sensing, could be used by the controller of the external bionic limb for the detection of gait phase, speed, terrain variation, and volitional user intent.

Although a prosthetic liner was described herein, it will be understood by those of ordinary skill in the art that any apparel, shoe, prosthesis, orthosis, or exoskeleton could employ these inventive steps. For example, an athletic shoe that comprises these same design features would comprise a liner, or sock, made from skin-like dielectric material with embedded force, shape, EMG, temperature and ultrasound sensing. The foot liner would have a spatially varying tensile modulus correlated to the underlying skin strain values caused by ankle flexion/extension and subtalar inversion/eversion. The foot liner would support electronics for signal conditioning, A/D conversion, and wireless communication to a receiving station on the outer layer of the shoe, a wristband, an electronic smart phone, or device. The variable-impedance intermediate shoe layer (corresponding to the socket 50 in FIG. 26) comprises spatially-varying viscoelastic properties correlated to the viscoelastic properties of the underlying ankle-foot tissues for perpendicular tissue compressions. Finally, the external, or outer shoe layer (corresponding to the carbon fiber element 52 in FIG. 26) would comprise an elastic composite material for the storage of elastic strain energy during foot strike in walking and running.

Moreover, FIG. 28 shows a liner design with integrated force, circumference and EMG sensors. Liner manufacture will comprise two separate measurement and fabrication steps: 1) measure the biological segment unloaded shape and the skin strain field at distinct joint poses; 2) design and fabricate a variable-compliant silicone liner having a thickness at each anatomical point that is inversely related to peak skin strain with embedded sensors and accompanying wire leads or conductive traces.

Step 1

Using standard photogrammetric tools, a model of skin strain as a function of anatomical location and joint pose is generated. Such a model is necessary to understand how the mechanical interface should move and stretch relative to the skin surface, so as to minimize shear forces and discomfort at the skin-interface junction. In this procedure, the biological limb is first marked with a matrix of small (~2 mm diameter), black-ink dots across the entire skin-surface area for which the interface is designed to interact. The specific anatomical location and distance between these dots need not be precise, but the resolution, or the number of dots per $cm^2$ is important, as this resolution defines the resolution of the resulting skin strain field. In addition, the resolution can be variable, providing the opportunity to further investigate deformation in certain areas. Next, separate poses, or joint postures of the biological segment of interest, are captured using photogrammetric tools. Using approximately 30 digital photographs for each limb pose, 3D models are generated. The coordinates of the black dots on the skin will then be marked and exported for analysis. The point clouds for each pose will be triangulated in a corresponding manner so the mapping of points to triangles is the same.

Figures 30A, 30B:
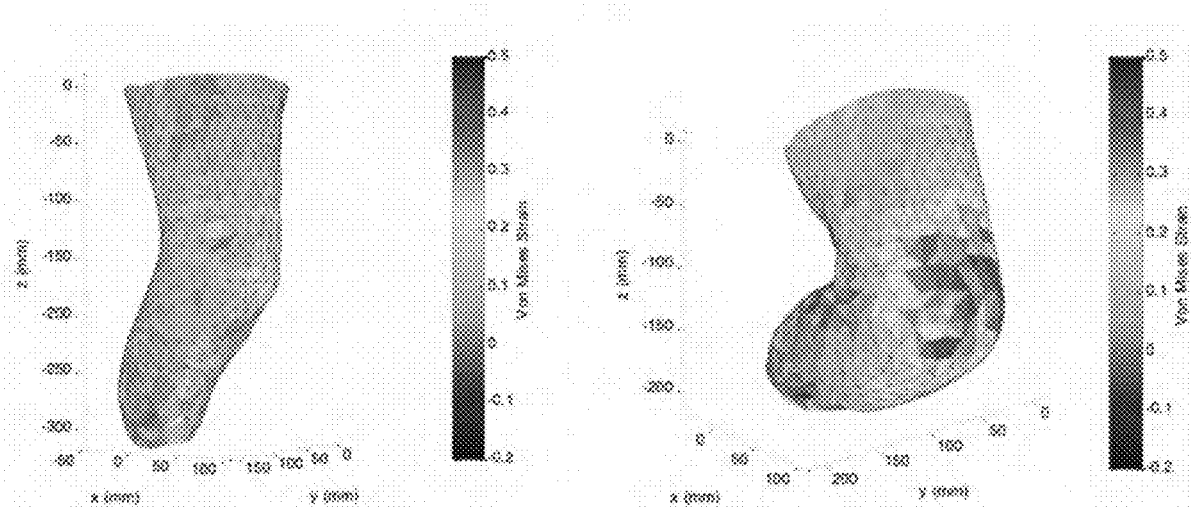
FIG. 30A shows the average strain of each triangular face being analyzed and mapped to a color with skin strain levels shown for the partially flexed pose.
FIG. 30B shows the average strain of each triangular face being analyzed and mapped to a color with skin strain levels shown for the fully flexed pose.

The black dots are the nodes of a finite element model and serve as the vertices for a surface triangulation. The deformation of each triangular element from one pose to another are then decomposed into a translation, rotation, and stretch via an affine transform. FIGS. 30A and 30B shows an example where the equivalent strain of each triangulation resulting from the deformation of the original, extended pose to two different levels of knee flexion, respectively. The average strain is a scalar value that is useful for assessing the overall stretch of a skin element. The average strain of each triangular face is analyzed and mapped to a color. Skin strain levels are shown for the partially flexed pose (FIG. 30A) and the fully flexed pose (FIG. 30B). Here higher average strain is shown around the knee patella due to the right pose's increased knee flexion.

Step 2

After the subject's skin strain has been measured, a variable-compliant silicone liner is fabricated having a tensile modulus at each anatomical point that is inversely proportional to the measured peak skin strain. Specifically, along directions where there is large skin strain, the adjacent liner will have a relatively low tensile modulus, whereas along skin directions where the skin strain is small the adjacent liner will have a relatively high tensile modulus. By varying the tensile compliance of the liner in this manner, shear forces are minimized at the liner-skin interface to mitigate skin damage and discomfort.

To fabricate such a variable-compliant liner, with integrated force, circumference and EMG sensors and their accompanying wire leads, a mold is 3-D printed having a negative space where silicone material is poured and allowed to cure. A male plug is 3-D printed with a shape corresponding to the unloaded biological segment of interest minus ~4 mm circumference reduction to achieve an appropriate liner tissue compression once fabricated. Further, as part of the same 3-D printing process, a female mold is fabricated around the male plug such that the gap separating the female and male 3-D printed parts is equal to the liner thickness. After printing, the wire leads, or conductive traces, and sensor volumes are placed into the mold prior to liner fabrication. For example, the EMG sensors are attached on the outer surface of the male plug at regions of residual limb musculature where EMG signal can be readily measured. Additionally, the grounding EMG electrode (e.g. EMG sensor 4 in FIG. 28) is placed on a boney protuberance of the male plug. Once the silicone material is poured within the gap separating male and female parts and has had adequate time to cure, the final silicone liner with embedded sensors and lead wires is removed from the mold and cleaned for use. To vary tensile modulus across the liner spatially, the liner thickness at each point could be varied, or the durometer of the silicone, or both. For the fabrication of a variable-durometer liner, separated cavities, or pockets, could be 3-D printed between the male and female molds, and within each cavity, silicone, with a distinct durometer, would then be injected and given time to cure.

In view of the above, an instrument for determining the anatomical, biomechanical, and physiological properties of a body segment that includes one or more force sensitive probes is provided. A human operator actuates one or more force sensitive probes, wherein the force sensitive probes are positioned at the surface of the body segment. The operator pushes on the force sensitive probes with varying force applied on the body segment to measure tissue deflection forces. The instrument may include one or more of gyroscopes, accelerometers, and magnetometers capable of measuring changes in tissue deflection caused by the force sensitive probes relative to a grounded reference frame in 3-D space, wherein the tissue deflection force data and the change in tissue deflection data are used to compute segment tissue viscoelastic properties. The instrument may be untethered or wireless.

It would be appreciated by those skilled in the art that various changes and modifications can be made to the illustrated embodiments without departing from the spirit of the present invention. All such modifications and changes are intended to be covered by the appended claims.

What is claimed is:

1. A system for determining anatomical, biomechanical, and physiological properties of a body segment, including an instrument, the instrument comprising:
   - one or more force sensitive probes configured and arranged for measuring tissue deflection forces upon application of varying forces applied on the body segment;
   - one or more inertial measurement units each of which include one or more of gyroscopes, accelerometers, and magnetometers configured and arranged for measuring changes in tissue deflection caused by the one or more force sensitive probes relative to a grounded reference frame in three-dimensional (3-D) space to create tissue deflection data; and
   - a controller configured to receive the tissue deflection force data and the tissue deflection data and configured to compute segment tissue viscoelastic properties as a function of the received tissue deflection force data and tissue deflection data, and one or more ultrasound probes positioned at a surface of the body segment configured and arranged to measure ultrasound data;

wherein the system is configured such that when an operator pushes on the one or more force sensitive probes with varying force on the body segment, the system is configured to measure at least one of tissue densities, nervous tissue transduction dynamics, blood flow, or soft tissue depths;

wherein the controller is configured to receive the tissue deflection force data and the ultrasound data and configured to compute the segment tissue viscoelastic properties as a function of the tissue deflection force data and the ultrasound data; and wherein the instrument is mechanically untethered.

2. A system for determining anatomical, biomechanical, and physiological properties of a body segment, including an instrument, the instrument comprising:

one or more force sensitive probes configured and arranged for measuring tissue deflection forces upon application of varying forces applied on the body segment;

one or more inertial measurement units each of which include one or more of gyroscopes, accelerometers, and magnetometers configured and arranged for performing a zero velocity update by holding the instrument stationary at a starting point on the body segment and then integrating forward to calculate a trajectory in three-dimensional (3-D) space relative to the starting point to create a grounded reference frame, and measuring changes in tissue deflection caused by the one or more force sensitive probes relative to the grounded reference frame in three-dimensional (3-D) space to create tissue deflection data; and a controller configured to receive the tissue deflection force data and the tissue deflection data and configured to compute segment tissue viscoelastic properties as a function of the received tissue deflection force data and tissue deflection data.

3. The system of claim 2, wherein the instrument is capable of wireless data transmission to a data receiver.

4. The system of claim 2, wherein the controller is configured and arranged to store the measured anatomical, biomechanical, and physiological data.

5. The system of claim 2, wherein the instrument is a handheld probe.

6. The system of claim 2, wherein the instrument is an array of probes.

7. The system of claim 2, wherein the one or more force sensitive probes measure force using one or more force sensors that are capacitive, resistive, piezoelectric based, strain-gauge based, or spring-potentiometer based.

8. The system of claim 2, wherein the instrument measures tissue stress or strain threshold where the subject first experiences discomfort.

9. The system of claim 2, wherein the instrument comprises at least one finger probe.

10. The system of claim 9, wherein the finger probe includes a finger socket which is configured to receive a finger of a user.

11. The system of claim 10, wherein the force probe is disposed on a tip of the finger socket.

12. The system of claim 10, wherein the finger socket further includes a flexible arm having a proximal end connected to the finger socket and a distal end connected to the inertial measurement unit.

13. The system of claim 2, further comprising:

one or more ultrasound transducers to measure internal tissue properties including tissue density and soft tissue depth.

14. The system of claim 13, wherein the one or more ultrasound transducers further measure blood flow in the body segment.

15. The system of claim 13, wherein the one or more ultrasound transducers further measure nervous tissue transduction dynamics.

* * * * *